US012697718B1

(12) United States Patent
Kathpal et al.

(10) Patent No.: US 12,697,718 B1
(45) Date of Patent: Aug. 4, 2026

(54) SYSTEM AND METHOD FOR CATEGORIZING UNSEGREGATED HEALTHCARE SUPPLIES INTO PREDEFINED STORAGE CHAMBERS USING HEALTHCARE SUPPLY METADATA

(71) Applicant: Inception Robotics, LLC, College Park, MD (US)

(72) Inventors: Abhishek Kathpal, College Park, MD (US); Adarsh Jagan Sathyamoorthy, Greenbelt, MD (US); Utsav Vishnubhai Patel, Greenbelt, MD (US); Dinesh Manocha, Bethesda, MD (US); Ujjwal Joshi, Jersey City, NJ (US)

(73) Assignee: Inception Robotics, LLC

( * ) Notice: Subject to any disclaimer, the term of this patent is extended or adjusted under 35 U.S.C. 154(b) by 0 days.

(21) Appl. No.: 19/441,910

(22) Filed: Jan. 7, 2026

Related U.S. Application Data

(60) Provisional application No. 63/743,884, filed on Jan. 10, 2025.

(51) Int. Cl.
*B25J 9/16* (2006.01)
*B25J 13/08* (2006.01)
(Continued)

(52) U.S. Cl.
CPC ........... *B25J 9/1612* (2013.01); *B25J 9/1633* (2013.01); *B25J 9/1664* (2013.01); *B25J 9/1669* (2013.01); *B25J 13/082* (2013.01);

*B25J 13/085* (2013.01); *B25J 19/023* (2013.01); *G06V 10/26* (2022.01); *G06V 10/82* (2022.01); *G06V 30/14* (2022.01);
(Continued)

(58) Field of Classification Search
CPC ...... B25J 9/1612; B25J 9/1633; B25J 9/1664; B25J 9/1669; B25J 13/082; B25J 13/085; B25J 19/023; G06V 10/26; G06V 10/82; G06V 30/14; G06V 2201/034; G06V 2201/10; G16H 40/40
See application file for complete search history.

(56) References Cited

U.S. PATENT DOCUMENTS

| | | | |
|---|---|---|---|
| 112,789 | A | 3/1871 | Denning |
| 828,155 | A | 8/1906 | Vittenet |

(Continued)

*Primary Examiner* — Harry Y Oh
(74) *Attorney, Agent, or Firm* — Jason C. Cameron

(57) ABSTRACT

A system and a method for categorizing unsegregated healthcare supplies into predefined storage chambers using healthcare supply metadata are disclosed. The system comprises an input container, robotic manipulators, an inspection chamber, inspection image capturing units, and storage chambers. The input container receives and retains the unsegregated healthcare supplies. The robotic manipulators move in at least three degrees of freedom for gripping and releasing a healthcare supply. The inspection chamber inspects the healthcare supply for extracting healthcare supply metadata. The inspection image capturing units capture multi-perspective healthcare supply images of the healthcare supply. The storage chambers are operatively coupled to a chamber positioning mechanism configured to selectively position the predefined storage chambers into an access position for receiving the healthcare supply from the robotic manipulators.

20 Claims, 12 Drawing Sheets

(51) Int. Cl.

| | | |
|---|---|---|
| *B25J 19/02* | (2006.01) |
| *G06V 10/26* | (2022.01) |
| *G06V 10/82* | (2022.01) |
| *G06V 30/14* | (2022.01) |
| *G16H 40/40* | (2018.01) |

(52) U.S. Cl.
CPC ....... *G16H 40/40* (2018.01); *G06V 2201/034*
(2022.01); *G06V 2201/10* (2022.01)

(56) References Cited

U.S. PATENT DOCUMENTS

| | | | | |
|---|---|---|---|---|
| 2014/0157731 | A1* | 6/2014 | Perazzo | B65B 57/02 |
| | | | | 141/2 |
| 2018/0082757 | A1* | 3/2018 | Chambers | G07F 11/165 |
| 2020/0061841 | A1* | 2/2020 | Davey | G06F 30/13 |
| 2020/0222284 | A1* | 7/2020 | Musini | A61J 7/0427 |
| 2023/0140779 | A1* | 5/2023 | Bouthiette | B65B 35/38 |
| | | | | 53/443 |
| 2025/0128416 | A1* | 4/2025 | Jones | B25J 15/0408 |

\* cited by examiner

100

106

108

102

104

120

122

110

112

114

118

116

400

Segregation stage start 402

Move segregation robotic manipulator towards the input container 404

Pickup logic 406

No

Inspection chamber region available? 408

Yes

Drop into the inspection chamber 410

End current segregation cycle 412

500

700

Sorting location assignment
702

Positioning sorting robotic
manipulator 704

Positioning storage chamber
706

Healthcare supply picking
from inspection chamber 708

Healthcare supply placement
in the storage chamber 710

800

| Receive, in an input container, the unsegregated healthcare supplies 802 |
| --- |

| Move one or more robotic manipulators configured with one or more actuators, one or more end-effectors, and one or more manipulator image capturing units, at least three degrees of freedom to grip and release at least one healthcare supply within the unsegregated healthcare supplies 804 |
| --- |

| Inspect, in an inspection chamber, the at least one healthcare supply from the input container to extract the healthcare supply metadata 806 |
| --- |

| Capture, by one or more inspection image capturing units, multi-perspective healthcare supply images of the at least one healthcare supply positioned on the inspection chamber 808 |
| --- |

| Obtain, by one or more hardware processors through a data obtaining subsystem, positional data, color data, depth data, the multi-perspective healthcare supply images, orientation data, storage chamber metadata, and pressure sensor data 810 |
| --- |

| Generate, by the one or more hardware processors through a manipulator triggering subsystem, a control command to trigger the one or more actuators for providing the motion to the one or more robotic manipulators based on the positional data, the color data and the depth data to reach towards the at least one healthcare supply in the input container 812 |
| --- |

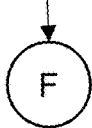

FIG. 8A

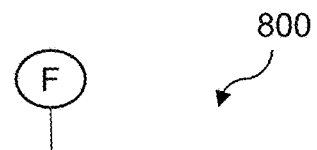

Operate, by the one or more hardware processors through an end-effector actuation subsystem, the one or more end-effectors based on the pressure sensor data to perform gripping and releasing of the at least one healthcare supply 814

Process, by the one or more hardware processors through a data extraction subsystem with one or more artificial intelligence (AI) models, the multi-perspective healthcare supply images to extract the healthcare supply metadata 816

Modify, by the one or more hardware processors through the manipulator triggering subsystem, the control command based on the orientation data to change an orientation of the at least one healthcare supply using the one or more robotic manipulators, to capture additional multi-perspective healthcare supply images 818

Map, by the one or more hardware processors through a data mapping subsystem, the extracted healthcare supply metadata with the storage chamber metadata associated with the plurality of storage chambers to determine the predefined storage chambers to receive the at least one healthcare supply 820

Operate, by the one or more hardware processors through a chamber actuating subsystem, the chamber positioning mechanism to actuate the predefined storage chambers into the access position for receiving the at least one healthcare supply 822

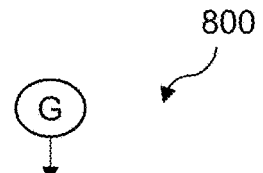

Generate, by the one or more hardware processors through the manipulator triggering subsystem, the control command to trigger the one or more actuators <u>824</u>

Provide, by the one or more hardware processors through the manipulator triggering subsystem, the motion to the one or more robotic manipulators based on the positional data associated with the predefined storage chambers to release the at least one healthcare supply into the predefined storage chambers to categorize the unsegregated healthcare supplies <u>826</u>

FIG. 8C

SYSTEM AND METHOD FOR CATEGORIZING UNSEGREGATED HEALTHCARE SUPPLIES INTO PREDEFINED STORAGE CHAMBERS USING HEALTHCARE SUPPLY METADATA

CROSS REFERENCE TO RELATED APPLICATION(S)

This application claims priority to provisional U.S. Patent Application No. 63/743,884 filed on Jan. 10, 2025, entitled, "A Cost-Effective, Portable Device for Sorting Healthcare Supplies and Devices", the disclosure of which is incorporated herein by reference in its entirety for all purposes"

TECHNICAL FIELD

Embodiments of the present disclosure relate to automation and robotics for material handling, and more particularly relate to a system, method, and device for categorizing unsegregated healthcare supplies into predefined storage chambers using healthcare supply metadata.

BACKGROUND

Healthcare facilities, pharmacies, and medical warehouses routinely manage a large volume of healthcare supplies that arrive in unsegregated form. One primary reason is a frequent return of healthcare supplies, with unused doses being sent back due to patient discharge, adjustments in treatment, and transfers. Returned healthcare supplies, including vials, syringes, unit doses, and pill packs, come jumbled together in large totes without any sorting. Because the healthcare supplies were originally dispensed in automated systems, their restocking requires manual re-grouping by technicians, a time-consuming, labor-intensive process. These healthcare supplies typically include medicines, medical consumables, and packaged products that differ in size, shape, dosage, batch number, and expiry date. Proper categorization and storage of such supplies are critical for ensuring traceability, maintaining quality standards, and preventing errors in supply distribution.

Conventional handling of healthcare supplies relies heavily on manual processes. Operators are required to inspect each healthcare supply visually, identify label information such as medicine name, dosage strength, lot number, expiry date, manufacturer identifier, or barcode/quick response (QR) code, and then place the healthcare supply into a corresponding storage chamber. Such manual sorting methods are labor-intensive, prone to human error, and inefficient when dealing with high-throughput environments such as hospitals, emergency care units, or large-scale pharmacies.

Some semi-automated systems exist that utilize barcode scanners or optical readers for identifying the healthcare supplies. Such semi-automated systems include handheld barcode scanners, fixed-position barcode reading stations, and optical label readers integrated into pharmacy workstations. However, these semi-automated systems are fundamentally limited because labels on many healthcare supplies do not encode critical information such as expiry date, pill count, batch number, or other clinically relevant details. As a result, even when a barcode is successfully scanned, the semi-automated systems may retrieve only a product identifier without complete metadata, needed for accurate categorization. Consequently, pharmacy staff must manually inspect the packaging to capture the missing information, leading to errors, inefficiencies, and incomplete automation.

Another drawback in existing technologies lies not only in manual storage infrastructure but also in the limitations of fully automated pharmacy systems, such as robotic dispensing units. The automated pharmacy systems require the healthcare supplies to be pre-sorted, pre-grouped, and provided in a highly standardized format before the healthcare supplies can be accepted into the automation workflow. The returned healthcare supplies and bulk, unsegregated healthcare supplies must therefore be manually reorganized by staff to match the automated pharmacy system's required input format. This dependency on strict packaging formats prevents such automated pharmacy systems from handling the diverse, mixed-orientation, and unstructured healthcare supply loads commonly encountered in real-world hospital and pharmacy environments.

Therefore, there exists a need for improved automation technologies that can efficiently handle unsegregated healthcare supplies, reliably extract metadata from labels under variable conditions, and accurately map the extracted metadata to predefined storage chambers without requiring extensive manual effort.

SUMMARY

This summary is provided to introduce a selection of concepts, in a simple manner, which is further described in the detailed description of the disclosure. This summary is neither intended to identify key or essential inventive concepts of the subject matter nor to determine the scope of the disclosure.

In accordance with an embodiment of the present disclosure, a system for categorizing unsegregated healthcare supplies into predefined storage chambers using healthcare supply metadata is disclosed.

In an embodiment, the system comprises an input container, one or more robotic manipulators, an inspection chamber, one or more inspection image capturing units, a plurality of storage chambers, one or more hardware processors, and a memory unit. In one aspect, the input container is configured to receive and retain the unsegregated healthcare supplies.

In other aspect, the one or more robotic manipulators are configured with one or more actuators, one or more end-effectors, and one or more manipulator image capturing units. The one or more robotic manipulators are configured to move in at least three degrees of freedom for gripping and releasing at least one healthcare supply from the unsegregated healthcare supplies in the input container. The at least three degrees of freedom are provided by the one or more actuators operatively coupled to a mechanical transmission assembly configured to generate the motion across multiple axes. The mechanical transmission assembly comprising at least one of: manipulator assembly, linkages, gear trains, cam systems, differential mechanisms, clutches, timing belts, and timing pulleys. The one or more actuators comprise at least one of: a stepper motor, a servo motor, a linear actuator, a pneumatic actuator, and a hydraulic actuator. The one or more end-effectors comprise at least one of: a suction-based gripper, a mechanical gripper, and a hybrid gripper.

In another aspect, the inspection chamber is operatively positioned proximate to the input container. The inspection chamber is configured to receive the at least one healthcare supply from the input container through the one or more robotic manipulators for inspecting the at least one healthcare supply for extracting the healthcare supply metadata. The inspection chamber is formed of a transparent material selected from a group comprises one of: glass, acrylic, polycarbonate, and transparent polymer, for enabling unobstructed multi-perspective imaging of the at least one healthcare supply by the one or more inspection image capturing units. The inspection chamber is operatively coupled to a rotating mechanism configured to rotate the inspection chamber about a predetermined axis for capturing the multi-perspective healthcare supply images of the at least one healthcare supply.

In yet another aspect, the one or more inspection image capturing units are operatively positioned at one or more defined angles with reference to the inspection chamber. The one or more manipulator image capturing units and the one or more inspection image capturing units comprise at least one of: a Red-Green-Blue (RGB) camera, a Red-Green-Blue with Depth (RGB-D) camera, a depth sensor, a stereo vision camera, a multi-spectral imaging camera, and a thermal imaging camera. The one or more inspection image capturing units are configured to capture the multi-perspective healthcare supply images of the at least one healthcare supply positioned on the inspection chamber.

In another aspect, the plurality of storage chambers is operatively positioned proximate to one of: the input container and the inspection chamber. Each storage chamber of the plurality of storage chambers is operatively coupled to a chamber positioning mechanism configured to selectively position the predefined storage chambers into an access position for receiving the at least one healthcare supply from the one or more robotic manipulators. The chamber positioning mechanism comprises at least one of: a linear sliding mechanism, a rotary carousel mechanism, a scissor-lift mechanism, a spring-loaded pop-out mechanism, and an elevator mechanism. Each storage chamber is configured with a unique chamber identifier. Each storage chamber with the unique chamber identifier is mapped with the storage chamber metadata. The storage chamber metadata comprises at least one of: a healthcare supply name, a dosage strength, a lot number, an expiry date, a manufacturer identifier, a barcode value, a quick response (QR) code value, and a healthcare supply category identifier, generated based on user-defined sorting rules input through a user interface.

In another aspect, the system comprises the one or more hardware processors and the memory unit operatively connected to the one or more hardware processors. The memory unit comprises a set of computer-readable instructions in the form of a plurality of subsystems, configured to be executed by the one or more hardware processors. The plurality of subsystems comprises a data obtaining subsystem, a manipulator triggering subsystem, an end-effector actuation subsystem, a data extraction subsystem, a data mapping subsystem, and a chamber actuating subsystem.

In one aspect, the data obtaining subsystem is configured to obtain positional data associated with the one or more robotic manipulators and the predefined storage chambers, color data and depth data from the one or more manipulator image capturing units, the multi-perspective healthcare supply images and orientation data from the one or more inspection image capturing units, storage chamber metadata associated with the plurality of storage chambers, and pressure sensor data associated with the one or more end-effectors. The positional data is obtained from one or more of: encoder feedback signals generated by encoders operatively associated with the one or more actuators, limit switch signals defining reference positions of the one or more robotic manipulators and the chamber positioning mechanism, step count data generated by actuator drives of the one or more actuators, and the depth data captured by the one or more manipulator image capturing units.

In another aspect, the manipulator triggering subsystem is configured to generate a control command to trigger the one or more actuators for providing a motion to the one or more robotic manipulators based on the positional data, the color data, and the depth data to reach towards the at least one healthcare supply in the input container. The manipulator triggering subsystem is further configured to process the positional data using a mathematical representation model to determine a current location of the one or more robotic manipulators. The manipulator triggering subsystem is further configured to process the color data and the depth data using a vision-based object detection model associated with one or more artificial intelligence (AI) models to determine a target location of the at least one healthcare supply within the input container. The manipulator triggering subsystem is further configured to generate the control command by computing a motion trajectory from the current location to the target location using a motion planning model associated with the one or more AI models. The motion planning model comprising at least one of: an inverse kinematics solver, a trajectory optimization model, and a reinforcement learning-based motion policy.

In another aspect, the end-effector actuation subsystem is configured to operate the one or more end-effectors based on the pressure sensor data for gripping and releasing the at least one healthcare supply. The end-effector actuation subsystem is further configured to process the pressure sensor data by monitoring vacuum levels in the suction-based gripper or gripping force in the mechanical gripper and comparing the monitored one of: the vacuum levels and the gripping force against predefined threshold values to verify successful gripping and releasing of the at least one healthcare supply. The end-effector actuation subsystem is further configured to modify the control command to initiate one of: a re-grasp sequence and a repositioning sequence based on: a) the pressure sensor data indicating one of: an ineffective gripping and releasing, and b) comparative analysis between one of: the vacuum levels and the gripping force against the predefined threshold values. The predefined threshold values generated based on historical pressure sensor data associated with the gripping of the unsegregated healthcare supplies.

In another aspect, the data extraction subsystem is configured with the one or more AI models to process the multi-perspective healthcare supply images for extracting the healthcare supply metadata. The one or more AI models comprise at least one of: an image segmentation model trained to segment label region on the multi-perspective healthcare supply images from nearby packaging information; an object detection model trained to localize alphanumeric text within the segmented label regions to extract the healthcare supply metadata; an optical character recognition (OCR) model trained to extract the alphanumeric text from the multi-perspective healthcare supply images; a barcode or quick response (QR) code recognition model to decode machine-readable identifiers for extracting the healthcare supply metadata; a vision-language model is configured to interpret at least one of: textual features and visual features in combination to extract the healthcare supply metadata; and a unit-count estimation model is configured to identify healthcare supply boundaries within the multi-perspective healthcare supply images for generating healthcare supply count data based on the identified healthcare supply boundaries.

In yet another aspect, the manipulator triggering subsystem is configured to modify the control command based on the orientation data to change the orientation of the at least one healthcare supply using the one or more robotic manipulators, to capture additional multi-perspective healthcare supply images when the previously captured images are inadequate to extract the healthcare supply metadata.

In another aspect, the data mapping subsystem is configured to map the extracted healthcare supply metadata with the storage chamber metadata associated with the plurality of storage chambers to determine the predefined storage chambers for receiving the at least one healthcare supply. The data mapping subsystem is further configured to perform the mapping by comparing the extracted healthcare supply metadata against the storage chamber metadata using at least one of: direct string-matching procedure, barcode matching procedure, quick response (QR) code matching procedure, numerical matching procedure, and fuzzy logic-based matching procedure of textual data. The data mapping subsystem is further configured to assign the at least one healthcare supply to a default storage chamber designated for unrecognized healthcare supplies when metadata correlation is absent. The data mapping subsystem is further configured to assign the at least one healthcare supply to a trash storage chamber if the extracted healthcare supply metadata indicates the at least one healthcare supply is one of: expired, damaged, excluded from restocking based on supply characteristics, and nominal consumed.

In another aspect, the chamber actuating subsystem is configured to operate the chamber positioning mechanism to actuate the predefined storage chambers into the access position for receiving the at least one healthcare supply based on mapping analysis performed by the data mapping subsystem between the extracted healthcare supply metadata and the storage chamber metadata. The manipulator triggering subsystem is further configured to generate the control command to trigger the one or more actuators. The one or more actuators provide the motion to the one or more robotic manipulators based on the positional data associated with the predefined storage chambers for releasing the at least one healthcare supply into the predefined storage chambers to categorize the unsegregated healthcare supplies.

In accordance with an embodiment of the present disclosure, a method for categorizing the unsegregated healthcare supplies into the predefined storage chambers using the healthcare supply metadata. In the first step, the method includes receiving, in the input container, the unsegregated healthcare supplies. In the next step, the method includes moving the one or more robotic manipulators configured with the one or more actuators, the one or more end-effectors, and the one or more manipulator image capturing units, the at least three degrees of freedom, to grip and release the at least one healthcare supply within the unsegregated healthcare supplies.

In the next step, the method includes inspecting, in the inspection chamber, the at least one healthcare supply from the input container to extract the healthcare supply metadata. In the next step, the method includes capturing, by the one or more inspection image capturing units, the multi-perspective healthcare supply images of the at least one healthcare supply positioned on the inspection chamber.

In the next step, the method includes obtaining, by the one or more hardware processors through the data obtaining subsystem, the positional data associated with the one or more robotic manipulators and the predefined storage chambers, the color data and the depth data from the one or more manipulator image capturing units and the one or more inspection image capturing units, the multi-perspective healthcare supply images and the orientation data from the one or more inspection image capturing units, the storage chamber metadata associated with the plurality of storage chambers, and the pressure sensor data associated with the one or more end-effectors. In the next step, the method includes generating, by the one or more hardware processors through the manipulator triggering subsystem, the control command to trigger the one or more actuators for providing the motion to the one or more robotic manipulators based on the positional data, the color data and the depth data to reach towards the at least one healthcare supply in the input container.

In the next step, the method includes operating, by the one or more hardware processors through the end-effector actuation subsystem, the one or more end-effectors based on the pressure sensor data to perform gripping of the at least one healthcare supply from the input container and the inspection chamber, and releasing the at least one healthcare supply in the inspection chamber and the predefined storage chambers. In the next step, the method includes processing, by the one or more hardware processors through the data extraction subsystem with one or more AI models, the multi-perspective healthcare supply images to extract the healthcare supply metadata In the next step, the method includes modifying, by the one or more hardware processors through the manipulator triggering subsystem, the control command based on the orientation data to change the orientation of the at least one healthcare supply using the one or more robotic manipulators, to capture the additional multi-perspective healthcare supply images if the multi-perspective healthcare supply images are inadequate to extract the healthcare supply metadata. In the next step, the method includes mapping, by the one or more hardware processors through the data mapping subsystem, the extracted healthcare supply metadata with the storage chamber metadata associated with the plurality of storage chambers to determine the predefined storage chambers to receive the at least one healthcare supply.

In the next step, the method includes operating, by the one or more hardware processors through the chamber actuating subsystem, the chamber positioning mechanism to actuate the predefined storage chambers into the access position for receiving the at least one healthcare supply based on mapping analysis performed by the data mapping subsystem between the extracted healthcare supply metadata and the storage chamber metadata. In the next step, the method includes generating, by the one or more hardware processors through the manipulator triggering subsystem, the control command to trigger the one or more actuators. In the next step, the method includes providing, by the one or more hardware processors through the manipulator triggering subsystem, the motion to the one or more robotic manipulators based on the positional data associated with the predefined storage chambers to release the at least one healthcare supply into the predefined storage chambers to categorize the unsegregated healthcare supplies.

According to another embodiment of the present disclosure, a non-transitory computer-readable storage medium storing the computer-readable instructions that, when executed by the one or more hardware processors, cause the one or more hardware processors to perform operations for categorizing the unsegregated healthcare supplies into the predefined storage chambers using the healthcare supply metadata, the operations comprising: a) obtaining the positional data associated with the one or more robotic manipulators and the predefined storage chambers, the color data and the depth data from the one or more manipulator image capturing units and the one or more inspection image capturing units, the multi-perspective healthcare supply images and the orientation data from the one or more inspection image capturing units, the storage chamber metadata associated with the plurality of storage chambers, and the pressure sensor data associated with the one or more end-effectors; b) generating the control command to trigger the one or more actuators for providing motion to the one or more robotic manipulators based on the positional data, the color data and the depth data to reach towards the at least one healthcare supply within the unsegregated healthcare supplies in the input container; c) operating the one or more end-effectors based on the pressure sensor data to perform gripping of the at least one healthcare supply from the input container and the inspection chamber, and releasing the at least one healthcare supply in the inspection chamber and the predefined storage chambers within the plurality of storage chambers; d) processing with the one or more AI models the multi-perspective healthcare supply images to extract the healthcare supply metadata; e) modifying the control command based on the orientation data to change the orientation of the at least one healthcare supply using the one or more robotic manipulators, to capture the additional multi-perspective healthcare supply images if the multi-perspective healthcare supply images are inadequate to extract the healthcare supply metadata; f) mapping the extracted healthcare supply metadata with the storage chamber metadata associated with the plurality of storage chambers to determine the predefined storage chambers to receive the at least one healthcare supply; g) operating the chamber positioning mechanism to actuate the predefined storage chambers into the access position for receiving the at least one healthcare supply based on mapping analysis between the extracted healthcare supply metadata and the storage chamber metadata; h) generating the control command to trigger the one or more actuators; and i) providing the motion to the one or more robotic manipulators based on the positional data associated with the predefined storage chambers to release the at least one healthcare supply into the predefined storage chambers to categorize the unsegregated healthcare supplies.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF DRAWINGS

The disclosure will be described and explained with additional specificity and detail with the accompanying figures in which:

FIG. 8A-8C illustrates an exemplary flow chart of a method for categorizing the unsegregated healthcare supplies into the predefined storage chambers using healthcare supply metadata, in accordance with an embodiment of the present disclosure.

Figure 1A:
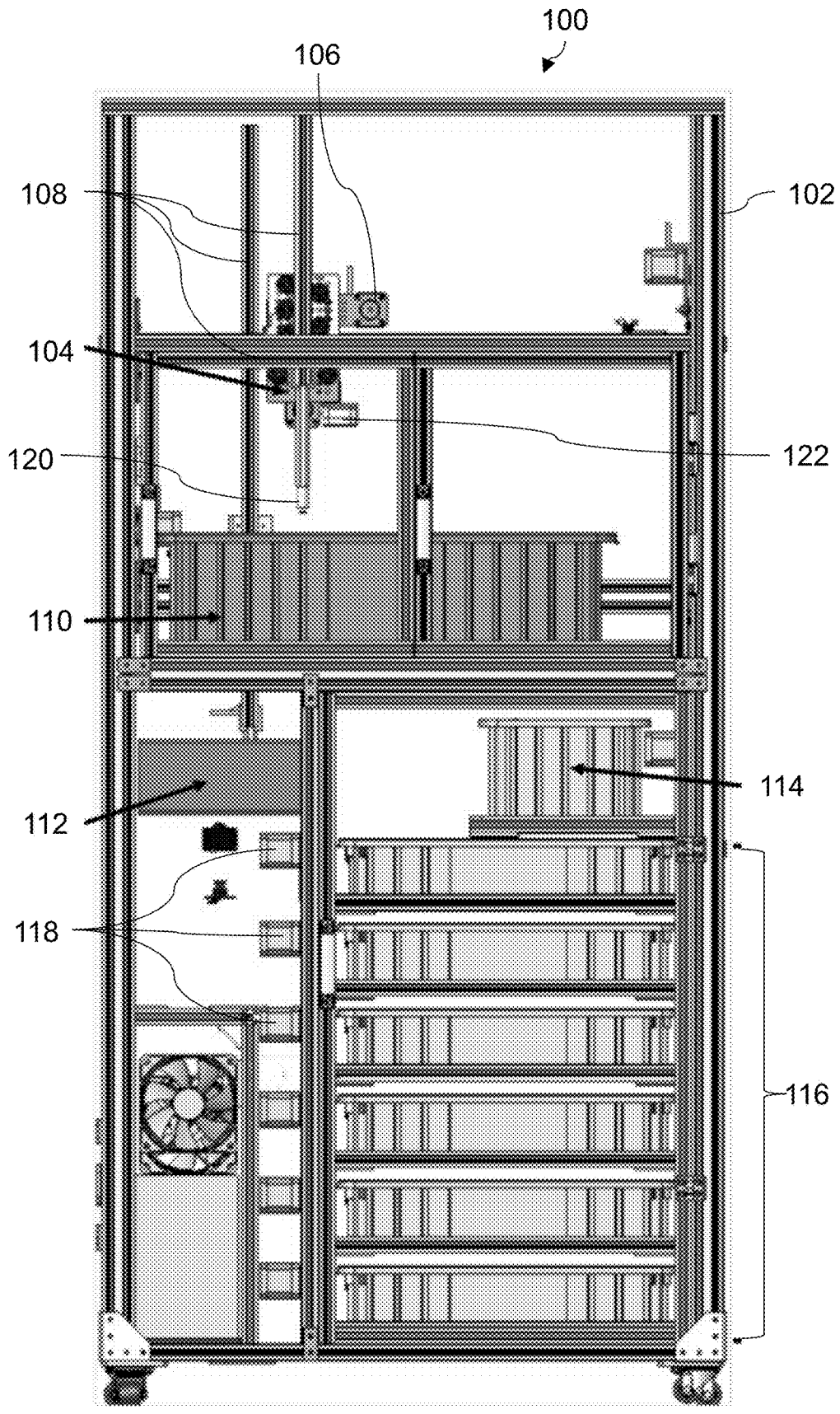
FIG. 1A illustrates an exemplary front view of a system for categorizing unsegregated healthcare supplies into predefined storage chambers using healthcare supply metadata, in accordance with an embodiment of the present disclosure.

Further, those skilled in the art will appreciate that elements in the figures are illustrated for simplicity and may not have necessarily been drawn to scale. Furthermore, in terms of the construction of the system or device, one or more components of the system or device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION OF THE DISCLOSURE

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure. It will be understood by those skilled in the art that the foregoing general description and the following detailed description are exemplary and explanatory of the disclosure and are not intended to be restrictive thereof.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

The terms "comprise", "comprising", or any other variations thereof, are intended to cover a non-exclusive inclusion, such that one or more devices or sub-systems or elements or structures or components preceded by "comprises . . . a" does not, without more constraints, preclude the existence of other devices, sub-systems, additional submodules. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

A computer system (standalone, client or server computer system) configured by an application may constitute a "module" (or "subsystem") that is configured and operated to perform certain operations. In one embodiment, the "module" or "subsystem" may be implemented mechanically or electronically, so a module includes dedicated circuitry or logic that is permanently configured (within a special-purpose processor) to perform certain operations. In another embodiment, a "module" or "subsystem" may also comprise programmable logic or circuitry (as encompassed within a general-purpose processor or other programmable processor) that is temporarily configured by software to perform certain operations.

Accordingly, the term "module" or "subsystem" should be understood to encompass a tangible entity, be that an entity that is physically constructed permanently configured (hardwired) or temporarily configured (programmed) to operate in a certain manner and/or to perform certain operations described herein.

Referring now to the drawings, and more particularly to FIG. 1 through FIG. 8C, where similar reference characters denote corresponding features consistently throughout the figures, there are shown preferred embodiments, and these embodiments are described in the context of the following exemplary system and/or method.

As used herein, the term "healthcare supply metadata" refers to structured information associated with a healthcare supply. The healthcare supply metadata is a complete set of descriptive, regulatory, and machine-readable information one of: printed on, encoded within, and digitally linked to the healthcare supply. The healthcare supply metadata enables automated detection, interpretation, and verification of the healthcare supply during inspection. The healthcare supply metadata serves as a basis for categorizing unsegregated healthcare supplies into predefined storage chambers.

FIG. 1A illustrates an exemplary front view of a system 100 for categorizing the unsegregated healthcare supplies into the predefined storage chambers 116 using healthcare supply metadata, in accordance with an embodiment of the present disclosure.

Figure 1B:
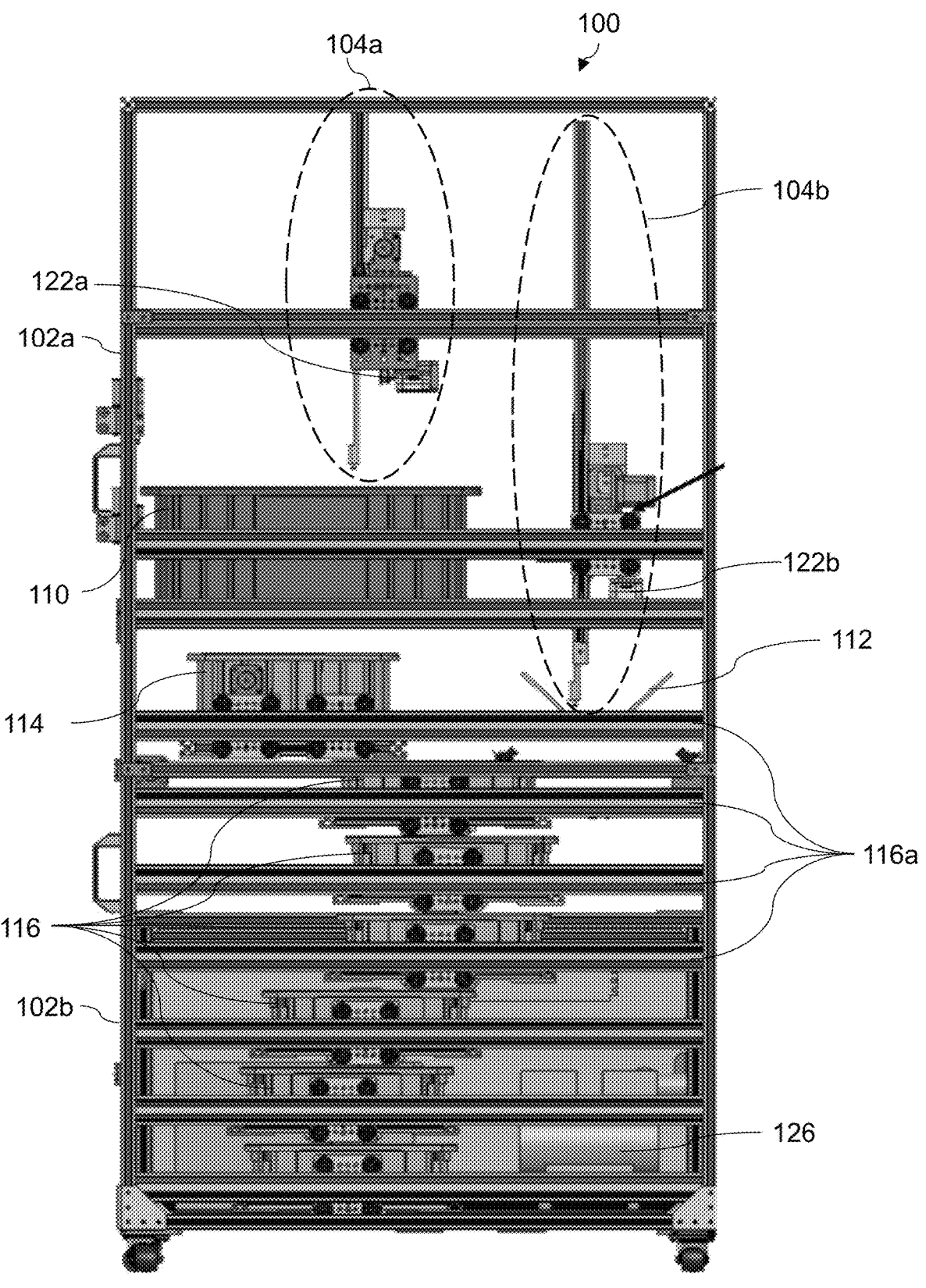
FIG. 1B illustrates an exemplary first side view of the system, in accordance with an embodiment of the present disclosure.

FIG. 1B illustrates an exemplary first side view of the system 100, in accordance with an embodiment of the present disclosure.

Figure 1C:
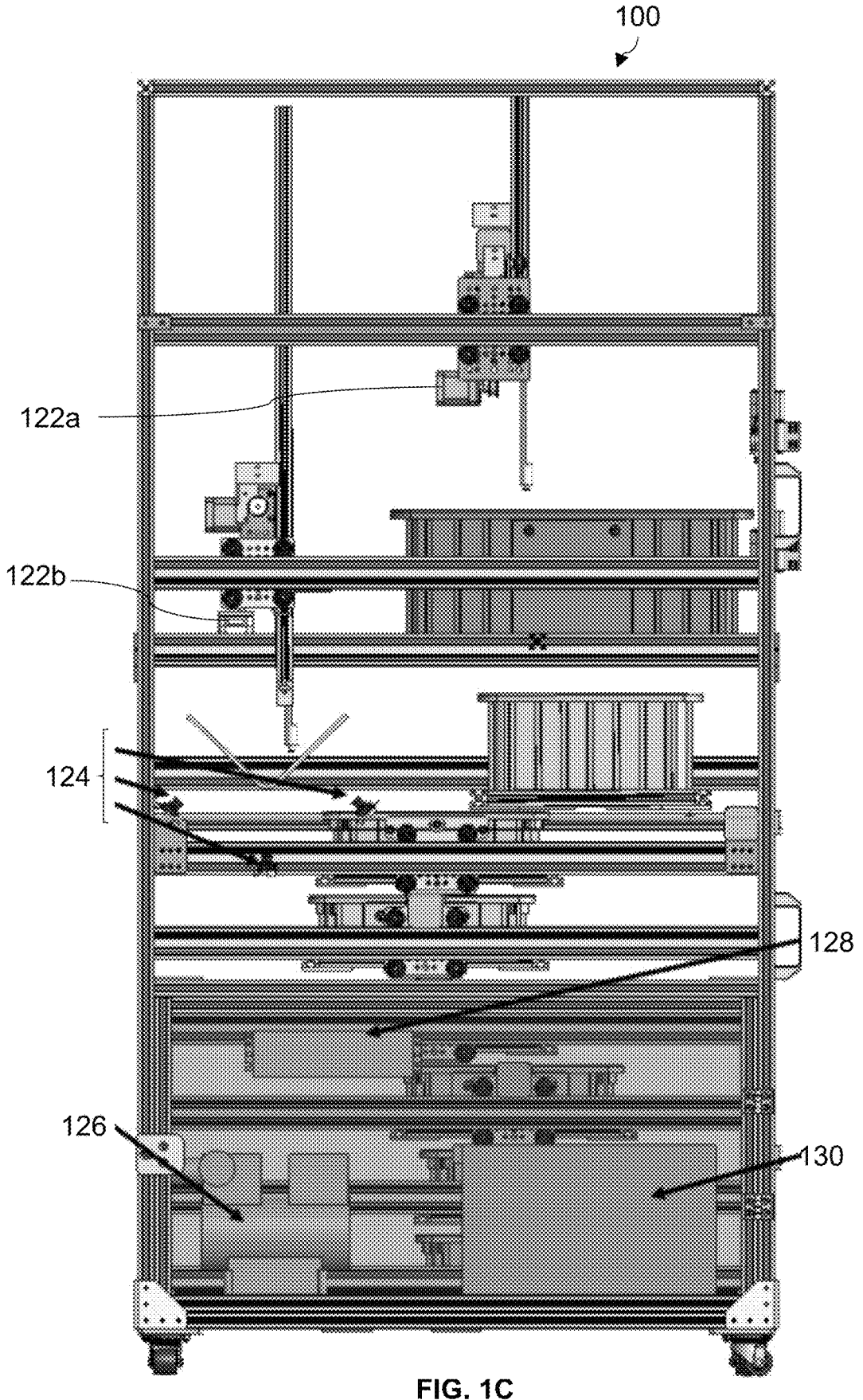
FIG. 1C illustrates an exemplary second side view of the system, in accordance with an embodiment of the present disclosure.

FIG. 1C illustrates an exemplary second side view of the system 100, in accordance with an embodiment of the present disclosure.

According to an exemplary embodiment of the present disclosure, the system 100 comprises a cabinet 102, an input container 110, one or more robotic manipulators 104, an inspection chamber 112, one or more manipulator image capturing units 122, one or more inspection image capturing units 124, a plurality of storage chambers 116, and a compute module housing 130.

In an exemplary embodiment, the unsegregated healthcare supplies may comprise, but not constricted to, at least one of: solid oral dosage forms such as tablets, capsules, and unit dose blister packs; liquid preparations like syrups, vials, and ampoules; injectable supplies including syringes, prefilled pens, and intravenous (IV) bags; and topical preparations such as ointment tubes, creams, and sprays. Each of the unsegregated healthcare supplies may be packaged in varying shapes and materials, for example, glass vials, plastic bottles, foil blister packs, and paper cartons, making the categorization challenging without automation. The system 100 is therefore configured to process such diverse healthcare supplies irrespective of size, form factor, and packaging geometry.

In an exemplary embodiment, the cabinet 102 houses and structurally integrates all system components in a compact and portable configuration. The cabinet 102 provides mechanical protection, stability, and operator safety by enclosing the input container 110, the inspection chamber 112, the one or more robotic manipulators 104, the plurality of storage chambers 116, and the compute module housing 130 within a single frame. The cabinet 102 may be fabricated from aluminum extrusions, sheet metal, or reinforced polymer panels to achieve both durability and reduced weight. The cabinet 102 further minimizes system footprint to enable deployment in diverse environments such as hospital pharmacies, long-term care facilities, and laboratories. For accessibility, the cabinet 102 may include hinged or sliding doors for loading healthcare supplies and retrieving storage chambers, transparent windows for inspection visibility, and dedicated compartments for wiring, ventilation, and power supply integration.

In an exemplary embodiment, the input container 110 is configured to retain the unsegregated healthcare supplies received from one or more users. The input container 110 is dimensioned to accommodate the unsegregated healthcare supplies of varying geometries, sizes, and packaging types. The input container 110 may be fabricated from rigid materials such as, but not restricted to, one of: stainless steel, aluminum, high-strength polymers, and the like, to provide durability and resistance against deformation under load.

In some embodiments, the input container 110 may further include one of: anti-slip lining and cushioning inserts to prevent damage to fragile unsegregated healthcare supplies during placement. The anti-slip lining, which may be formed from materials such as one of: silicone, textured rubber, and thermoplastic elastomers, increases surface friction within the input container 110 to prevent unintended sliding and shifting of the unsegregated healthcare supplies during loading and manipulator interaction. The cushioning inserts, which may include one of: foam pads, gel-based layers, and shock-absorbing polymer sheets, are configured to absorb impact forces and vibrations, thereby minimizing the risk of cracks, leaks, and deformation in fragile healthcare supplies. Together, these protective features maintain the integrity of the unsegregated healthcare supplies while improving stability and reliability during a segregation process.

The input container 110 is positioned within the cabinet 102 of the system 100 using a first door 102*a*. The first door 102*a* enables loading of the input container 110 configured with the unsegregated healthcare supplies into the cabinet 102 while maintaining enclosure integrity of the system 100. The unsegregated healthcare supplies deposited into the input container 110 remain retained until accessed by a segregation robotic manipulator 104a of the one or more robotic manipulators 104. In another aspect, the input container 110 may optionally include one of: orientation guides and passive alignment features to prevent the unsegregated healthcare supplies from stacking in unstable positions. The orientation guides, such as one of: angled walls, ridges, and grooves, provide directional constraints that naturally steer the unsegregated healthcare supplies into more uniform orientations, thereby simplifying downstream gripping and inspection. The passive alignment features, which may include at least one of: tapered surfaces, V-shaped channels, and contoured dividers, enable the unsegregated healthcare supplies to settle into predictable resting positions without requiring active control, thereby reducing the likelihood of healthcare supply stacking in unstable configurations. The input container 110 thus serves as a primary receptacle for receiving bulk, unorganized healthcare supplies and retaining the unsegregated healthcare supplies securely until the unsegregated healthcare supplies are individually picked, inspected, and categorized by the system 100.

In another exemplary embodiment, the one or more robotic manipulators 104 are configured with, but not restricted to, one or more actuators 106, one or more end-effectors 120, one or more manipulator image capturing units 122, and the like. The system 100 utilizes a plurality of controller units (e.g., microcontrollers or microprocessors) for coordinating system operations. The plurality of controller units is employed for controlling the motion of the one or more robotic manipulators 104 as well as regulating the positions of the plurality of storage chambers 116 and actuating vacuum switches. The plurality of controller units ensures precise handling of at least one healthcare supply by synchronizing manipulator movements, compartment positioning, and suction control at the one or more end-effectors 120.

The one or more robotic manipulators 104 are configured to move in at least three degrees of freedom for gripping and releasing the at least one healthcare supply from the unsegregated healthcare supplies in the input container 110. The degrees of freedom refer to independent motions possible by the one or more robotic manipulators 104 along translational and rotational axes. The at least three degrees of freedom may include, by way of example, linear movement along an X-axis and Y-axis, combined with a vertical movement along a Z-axis, and a rotational motion about one or more of the X-axis, Y-axis, and Z-axis. Such multi-axis mobility enables the one or more robotic manipulators 104 to accurately reach, orient, and position the unsegregated healthcare supplies of varying shapes and orientations within the input container 110.

The at least three degrees of freedom are provided by the one or more actuators 106, which are operatively coupled to a mechanical transmission assembly 108 to generate the motion across multiple axes. The mechanical transmission assembly 108 refers to mechanical components configured to convert actuator motion into controlled multi-axis manipulator motion. The mechanical transmission assembly 108 comprises, but not restricted to, at least one of: manipulator assembly, linkages, gear trains, cam systems, differential mechanisms, clutches, timing belts, timing pulleys, and the like.

The manipulator assembly is one of: an integrated robotic arm and gantry structure comprising interconnected links and joints that provide spatial mobility to the one or more robotic manipulators 104. For example, a Cartesian gantry system with three linear actuators may provide X, Y, and Z motion. The linkages are rigid mechanical bars connected through pivot joints to transfer and transform input motion into desired output motion. For instance, a four-bar linkage may amplify and redirect linear actuator displacement to achieve rotation. The gear trains are a series of gears meshed to transmit torque and modify speed and direction of actuator output. For example, a spur gear train may be used to achieve rotational degrees of freedom for the one or more robotic manipulators 104.

The cam systems are mechanical systems using cams and followers to transform rotary motion into one of: linear motion. For example, a cam profile may generate controlled vertical displacement for positioning the unsegregated healthcare supplies. The differential mechanisms are gear-based systems that one of: split and combine motion between two or more outputs. For instance, a differential mechanism may distribute torque from a single actuator 106 of the one or more actuators 106 to drive the one or more robotic manipulators 104 simultaneously.

The clutches are mechanical devices used to selectively one of: engage and disengage actuator power transmission to the one or more robotic manipulators 104. For example, an electromagnetic clutch may allow switching between linear and rotary motion modes. The timing belts and timing pulleys are belt-and-pulley mechanisms with toothed belts that provide synchronized, backlash-free transmission of actuator motion to manipulator axes. For example, timing belts may be used to achieve precise X-Y travel.

The one or more actuators 106 may include, but not limited to, at least one of: a stepper motor, a servo motor, a linear actuator, a pneumatic actuator, a hydraulic actuator, and the like. The stepper motor is an electromechanical actuator that divides a full rotation into a discrete number of steps, enabling precise positioning without continuous feedback. The stepper motors may be used to control linear motion along an axis. The servo motor provides closed-loop control of angular and linear position using encoder feedback. The servo motors are employed for providing accurate orientation control of the one or more end-effectors 120.

The linear actuator directly produces linear displacement, driven by one of: lead screws, ball screws, and electric motors. The linear actuators may be used to one of: extend and retract the one or more robotic manipulators 104 along the Z-axis. The pneumatic actuator is powered by compressed air to generate rapid one of: linear and rotary motion, used for lightweight, high-speed one or more robotic manipulators 104. The hydraulic actuator is a high-force actuator using pressurized fluid, suitable for heavy-duty gripping and lifting of larger healthcare supplies.

In some alternative exemplary embodiments, the system 100 may incorporate more than one robotic manipulator 104 during at least one of: a segregation stage and a sorting stage to enable parallelization of operations. A plurality of segregation robotic manipulators 104a working simultaneously within the input container 110 accelerate the isolation of the at least one healthcare supply from a bulk collection, thereby improving throughput and reducing processing time. A plurality of sorting robotic manipulators 104b working simultaneously within the inspection chamber accelerate orientation, repositioning, and placement of the at least one healthcare supply. The system 100 may be configured with a single robotic manipulator 104 to perform both segregation and sorting functions. This dual-purpose configuration avoids interference between the robotic manipulators 104 in the restricted workspace of storage chamber region and ensures precise categorization of the unsegregated healthcare supplies. The system 100 may employ a modular manipulator configuration, where the one or more robotic manipulators 104 may be dynamically added and removed depending on processing demand. For example, in a high-throughput pharmacy setup, additional robotic manipulators 104 may be employed into the system 100 to scale capacity.

In an exemplary embodiment, the one or more end-effectors 120 are coupled to a distal end of the one or more robotic manipulators 104. The one or more end-effectors 120 are configured to interface with the healthcare supplies. The system 100 further comprises a vacuum pump 126 that generates negative pressure required for gripping the at least one healthcare supply via the one or more end-effectors 120. The vacuum pump 126 functions by creating a pressure differential between the one or more end-effectors 120 and surrounding atmosphere, thereby ensuring secure attachment of the at least one healthcare supply until release is triggered. The suction flow is controlled by the vacuum switches operatively coupled to the plurality of controller units. The vacuum switches selectively connect the one or more end-effectors 120 to one of: the vacuum pump 126 and vent the one or more end-effectors 120 to the atmosphere. During gripping, the vacuum switches connect the one or more end-effectors 120 to the vacuum pump 126, enabling secure handling of the at least one healthcare supply. During release, the vacuum switches vent the one or more end-effectors 120 to the atmosphere, thereby disengaging the at least one healthcare supply safely.

The one or more end-effectors 120 may comprise, but not constrained to, at least one of: a suction-based gripper, a mechanical gripper, a hybrid gripper, and the like. The suction-based gripper is a vacuum-driven gripper that creates the negative pressure on the surface of the at least one healthcare supply to lift and hold the at least one healthcare supply. For example, suction cups may grip flat surfaces of medicine blister packs.

The mechanical gripper is configured with one of: jaws and fingers that physically enclose and clamp the at least one healthcare supply. For example, parallel jaw grippers may hold cylindrical vials and bottles. The hybrid gripper is a combination of suction and mechanical gripping elements, enabling adaptability across the healthcare supplies with diverse geometries and surface properties. For instance, the hybrid gripper may use suction for flat cartons and the fingers for irregular-shaped syringes. The one or more robotic manipulators 104 are configured to dynamically grip, orient, and release the unsegregated healthcare supplies with accuracy and reliability, thereby supporting downstream inspection and categorization processes.

In an exemplary embodiment, the inspection chamber 112 is operatively positioned proximate to the input container 110. The inspection chamber 112 is configured to receive the at least one healthcare supply from the input container 110 through the one or more robotic manipulators 104 for inspecting the at least one healthcare supply to extract the healthcare supply metadata. The healthcare supply metadata may include, but not limited to, at least one of: healthcare supply name, dosage strength, lot number, expiry date, manufacturer identifier, barcode value, quick response (QR) code value, supply category identifier, healthcare supply count data, and the like.

The inspection chamber 112 is formed of a transparent material, selected from a group comprising, but not constrained to, one of: glass, acrylic, polycarbonate, transparent polymer, and the like. The transparency of the inspection chamber 112 allows the one or more inspection image capturing units 124 to obtain unobstructed, distortion-free images of the at least one healthcare supply from multiple viewing angles. For instance, the glass provides optical clarity and scratch resistance for accurate imaging. The acrylic is lightweight and impact resistant, suitable for high-throughput systems. The polycarbonate provides superior impact strength and resistance to shattering, which is advantageous for handling heavy and fragile medical packages. The transparent polymers may be tailored for anti-glare and anti-reflection properties, improving image quality in varying lighting conditions.

In some embodiments, the inspection chamber 112 may further incorporate anti-reflective coatings and internal diffusers to minimize optical distortions and shadows that could interfere with image processing. The anti-reflective coatings are applied on transparent surfaces to minimize glare and light reflections, thereby ensuring accurate capture of label and packaging details. The internal diffusers are optical elements configured to scatter and evenly distribute illumination inside the inspection chamber 112, reducing harsh shadows and minimizing optical distortions. Together, these features enhance the quality and consistency of multi-perspective images, thereby improving the performance of downstream image processing and metadata extraction.

In an exemplary embodiment, the inspection chamber 112 is operatively coupled to a rotating mechanism. The rotating mechanism is configured to rotate the inspection chamber 112 about a predetermined axis. This rotation allows the at least one healthcare supply placed inside the inspection chamber 112 to be captured from multiple perspectives by the one or more inspection image capturing units 124. The rotating mechanism may include, but not restricted to, at least one of:

a) a rotary motor with a shaft for continuous 360° rotation of the inspection chamber 112. The rotary motor receives one of: pulse-width modulation (PWM) and analog control signals from the plurality of controller units, which regulate rotation speed and direction for precise alignment during image capture;

b) a stepper motor-driven turntable for discrete angular increments, such as 90° or 180°, enabling systematic label capture. The plurality of controller units transmits step and direction commands to a motor driver, ensuring precise incremental positioning with feedback from one of: limit switches and encoders;

c) gear and pulley arrangements to achieve smooth and synchronized rotation. A motor driving the gear/pulley setup is commanded by the plurality of controller units, which adjusts speed and torque via motor driver signals for controlled rotation; and d) bearings and support frames to provide stability during rotation and prevent vibration-induced image artifacts; and the like.

In another exemplary embodiment, the inspection chamber 112 may be in a V-shaped configuration and may be actuated to dynamically alter the geometry. In one mode, the inspection chamber 112 transforms into a flat surface for stable placement of two-dimensional healthcare supplies such as tablet strips, sachets, and blister packs. In another mode, the inspection chamber 112 reverts to a curved V-shape to naturally cradle cylindrical healthcare supplies such as the glass vials, the prefilled pens, or the syringes, ensuring consistent orientation for imaging. The inspection chamber 112 may take alternative geometrical shapes such as a flat tray, a U-shaped groove, and a bowl-shaped cavity. Each shape supports a different category of healthcare supplies: The flat trays for the blister packs, the U-shaped grooves for elongated syringes, and the bowl-shaped cavities for small, rounded containers such as ointment jars and ampoules. In another embodiment, the inspection chamber 112 may be omitted entirely. Instead, a multi-camera array may capture the at least healthcare supply in mid-air as the at least healthcare supply is held and rotated by the segregation robotic manipulator 104*a*. This eliminates the need for physical placement and is particularly useful for fragile and deformable healthcare supplies that may not rest stably in the inspection chamber 112.

In an exemplary embodiment, the one or more inspection image capturing units 124 are operatively positioned at one or more defined angles with reference to the inspection chamber 112. The angular positioning allows the one or more inspection image capturing units 124 to obtain multiple perspectives of the at least one healthcare supply placed within the inspection chamber 112. Such multi-perspective imaging is essential for accurate recognition of labels configured with the healthcare supply metadata that may not be visible from a single orientation. The one or more inspection image capturing units 124 are positioned at the bottom of the inspection chamber 112 to capture underside views, ensuring that no critical metadata remains occluded during inspection. In an exemplary embodiment, the one or more defined angles refer to predetermined spatial orientations at which the one or more inspection image capturing units 124 are positioned relative to the inspection chamber 112. The one or more defined angles are strategically selected to ensure that the healthcare supply placed within the inspection chamber 112 can be captured from multiple perspectives, minimizing blind spots, distortions, and reflections. For instance, if the one or more inspection image capturing units 124 are positioned at bottom, top, or alongside the inspection chamber 112, the one or more defined angles are at least one of 45 degrees, 90 degrees, and 120 degrees.

The one or more manipulator image capturing units 122 and the one or more inspection image capturing units 124 comprise, but not constricted to, at least one of: a Red-Green-Blue (RGB) camera, a Red-Green-Blue with Depth (RGB-D) camera, a depth sensor (e.g., ultrasound sensor, infrared sensor, and light detection and ranging (lidar)), a stereo vision camera, a multi-spectral imaging camera, a thermal imaging camera, and the like. The one or more manipulator image capturing units 122 and the one or more inspection image capturing units 124 operate under coordinated instructions issued by the plurality of controller units. The plurality of controller units, based on workflow requirements, sends triggering signals to the respective one or more manipulator image capturing units 122 and the one or more inspection image capturing units 124 to capture color and depth images at precise moments during the gripping, transferring, and inspection stages.

The RGB camera is a standard digital imaging sensor that captures color images in visible light. The RGB camera is used to obtain high-resolution color images of the healthcare supplies, enabling visual inspection of printed labels and logos. For example, the RGB camera may capture the healthcare supply name and dosage strength from the blister pack.

The RGB-D camera combines RGB color imaging with depth sensing, using structured light and time-of-flight technology. In another embodiment, the RGB-D camera in conjunction with a semantic segmentation model, such as a Segment Anything Model (SAM), and a depth estimation model, may be employed to identify gripping points for the at least one healthcare supply of varied shapes and sizes. A semantic segmentation model is a computer vision model configured to partition an image into pixel-level regions, where each pixel is assigned a label corresponding to an object class (e.g., pill pack, vial, blister card).

The semantic segmentation model enables the system 100 to distinguish the at least one healthcare supply from the background and surrounding clutter, isolating the contours and surfaces of individual healthcare supplies for accurate robotic handling. For example, the semantic segmentation model identifies the exact outline of the blister pack lying in the input container 110, separating the blister pack from overlapping pill boxes and allowing the one or more robotic manipulators 104 to plan a precise pickup.

The depth estimation model is a type of computer vision model that estimates the distance of objects in a 2D image from the camera. The depth estimation model takes a standard image as input and outputs a depth map, which is a grayscale or color-coded image where the brightness or color of each pixel represents the distance of the corresponding point in the real world. For example, in a grayscale depth map, darker shades often represent closer objects, and lighter shades represent farther objects. The depth estimation model computes the distance of each pixel in the image, thereby creating a depth map of the scene. The depth estimation model determines the three-dimensional (3D) orientation, height, and pickup feasibility of the healthcare supplies, ensuring the one or more robotic manipulators 104 apply the correct gripping force and angle. For example, the depth estimation model measures that the syringe is lying flat at the bottom of the input container 110, assisting the one or more robotic manipulators 104 in adjusting an end-effector trajectory to approach from the correct angle.

The SAM is a foundation vision model configured to generate segmentation masks for arbitrary objects in the image, even for unseen healthcare supplies. The SAM, when applied with RGB-D images, automatically segments unfamiliar and diverse healthcare supplies without retraining, making the SAM well-suited for handling mixed, unsegregated healthcare supplies. The SAM identifies the healthcare supplies. For instance, the SAM generates a mask around an IV bag despite glare and overlapping healthcare supplies, allowing the one or more robotic manipulators 104 to locate a suction-compatible flat area for pickup.

The RGB-D cameras provide both color images and 3D depth maps, enabling the system 100 to recognize label placement and supply orientation. For instance, the RGB-D camera may determine the spatial tilt of the vial to assist in reorientation.

The depth sensor directly measures distance to surfaces, using one of: laser triangulation and infrared projection. In the laser triangulation, a laser beam is projected onto the surface, and the reflected spot is captured by a detector at a known angle to calculate depth using trigonometric principles. In the infrared projection, a structured infrared light pattern is projected onto the surface, and the distortion is analyzed by the one or more manipulator image capturing units 122 to compute a depth map. The depth sensors provide precise 3D spatial data, which may be used to distinguish overlapping healthcare supplies and to determine the exact contour of irregular packaging.

The stereo vision camera is a pair of cameras arranged with a fixed baseline to simulate binocular vision. The stereo vision cameras estimate depth by comparing disparities between two camera images. The stereo vision camera is advantageous for calculating the relative position of the labels on curved and angled surfaces, such as bottles and cylindrical tubes.

The multi-spectral imaging camera is capable of capturing the images across multiple spectral bands beyond visible light, such as near-infrared and ultraviolet. The multi-spectral imaging camera enhances contrast of faint, faded, and low-visibility printed text on packaging. For example, invisible ink security markings on pharmaceutical labels may be detected by the multi-spectral imaging camera.

The thermal imaging camera captures infrared radiation to generate a thermal profile of the healthcare supply. The thermal camera may be used for non-visual metadata capture, such as identifying temperature-sensitive supplies, and ensuring that the inspection environment maintains proper thermal conditions for sensitive drugs.

The one or more inspection image capturing units 124 are configured to capture the multi-perspective healthcare supply images of the at least one healthcare supply positioned on the inspection chamber 112. The multi-perspective imaging ensures that all critical metadata elements are captured regardless of supply orientation and partial occlusion.

In some embodiments, additional inspection image capturing units 124 may be introduced into the system 100 to handle the at least one healthcare supply with complex and irregular form factors, such as the blister packs with reflective surfaces, cylindrical vials, and curved syringes. By increasing the number of inspection image capturing units 124, blind spots are reduced, enabling more robust metadata extraction across varying geometries. The one or more inspection image capturing units 124 surrounding the inspection chamber 112 may be actuated with linear and rotary stages to allow dynamic repositioning. This enables flexible viewing angles for the at least one healthcare supply with irregular packaging (e.g., folded leaflets attached to bottles or reflective foil packs) and provides redundancy in case of glare, shadowing, and occlusion.

In an exemplary embodiment, the plurality of storage chambers 116 is operatively positioned proximate to one of: the input container 110 and the inspection chamber 112, such that the at least one healthcare supply after inspection may be efficiently deposited into the predefined storage chambers 116 of the plurality of storage chambers 116 without excessive manipulator travel. Each storage chamber 116 of the plurality of storage chambers 116 is operatively coupled to a chamber positioning mechanism 118, which is configured to selectively position the predefined storage chamber 116 into an access position for receiving the at least one healthcare supply from the sorting robotic manipulator 104b. The access position is defined as an alignment of the predefined storage chamber 116 wherein the opening is spatially accessible to the one or more robotic manipulators 104 for depositing the at least one healthcare supply. As an illustrative example, in a linear sliding mechanism, the access position corresponds to the chamber sliding outward along a slider 116a until exposed to the one or more end-effectors 120. The chamber positioning mechanism 118 is defined as a mechanical system responsible for moving the plurality of storage chambers 116 between a rest position and the access position upon receiving instructions from the plurality of controller units.

The chamber positioning mechanism 118 comprises, but not constricted to, at least one of: the linear sliding mechanism, a rotary carousel mechanism, a scissor-lift mechanism, a spring-loaded pop-out mechanism, an elevator mechanism, and the like. The linear sliding mechanism moves the plurality of storage chambers 116 along the slider 116a in a straight line, enabling a tray-like chamber to slide forward for access. The rotary carousel mechanism rotates the plurality of storage chambers 116 mounted on a circular frame, similar to a rotating medicine carousel. The scissor-lift mechanism uses crossed linkages to at least one of:

horizontally slide and vertically raise and lower the plurality of storage chambers 116 to the access position.

The spring-loaded pop-out mechanism employs a biasing spring to project the plurality of storage chambers 116 outward when triggered, simplifying retrieval. The elevator mechanism is configured to slide or raise and lower the predefined storage chamber 116 along a horizontal axis or a vertical axis, respectively. The elevator mechanism is actuated after the predefined storage chamber 116 is deployed outward using one of the above-described mechanisms, such as the linear sliding mechanism and the spring-loaded pop-out mechanism. The elevator mechanism ensures that the predefined storage chamber 116 is positioned at the correct vertical height and the access position for interaction with the one or more robotic manipulators 104.

Each storage chamber 116 is configured with a unique chamber identifier, such as at least one of: a numeric code, a Radio Frequency Identification (RFID) tag, and a digital index, which allows the system 100 to uniquely recognize and access each storage chamber 116. Each storage chamber 116 with the unique chamber identifier is mapped with storage chamber metadata, ensuring the unsegregated healthcare supplies are consistently categorized. The storage chamber metadata comprises, but not restricted to, at least one of: a healthcare supply name (e.g., Paracetamol), a dosage strength (e.g., 500 milligrams), a lot number (e.g., L20240901), an expiry date (e.g., September 2026), a manufacturer identifier (e.g., MFG1234), a barcode value, a QR code value, a healthcare supply category identifier (e.g., antibiotics, pain relievers, and surgical supplies), and the like. The storage chamber metadata is generated and assigned based on user-defined sorting rules input through a user interface associated with one or more end devices and the system 100. For example, a sorting rule may specify: "assign all 500 mg Paracetamol tablets to storage chamber 3, tray 2, x=5, y=7, and z=2" or "route all expired supplies to storage chamber 4, tray 1, x=6, y=2, and z=1." The user-defined sorting rules ensure that the categorization process reflects real-world medical inventory management needs, including compliance, traceability, and segregation.

In an exemplary embodiment, each storage chamber 116 is configured with a plurality of compartments, each acting as a dedicated slot for organizing and holding the healthcare supplies according to the category. The structured layout not only improves retrieval efficiency but also prevents cross-contamination and accidental mixing of the healthcare supplies of different categories. For example, one compartment of the plurality of compartments may store pill blister packs and another for syringes.

In an illustrative exemplary embodiment, the system 100 comprises six storage chambers 116, each subdivided into eight individual compartments for organized storage of the segregated healthcare supplies. To optimize spatial efficiency, the plurality of storage chambers 116 is stacked vertically, reducing the overall system footprint. Each storage chamber 116 is mounted on the slider 116a, actuated by the stepper motors, allowing selective retrieval of the predefined storage chamber 116. This configuration of actuated sliding storage chambers 116 contributes to the compactness and operational efficiency of the system 100.

In an exemplary embodiment, a second door 102b is provided in the system 100 to enable access to the plurality of storage chambers 116. Through the second door 102b, the categorized healthcare supplies placed in the plurality of storage chambers 116 may be collected. The second door 102b allows removal and replacement of the plurality of storage chambers 116 without interrupting ongoing operations. This configuration ensures user-friendly retrieval, safe handling, and efficient replenishment of the plurality of storage chambers 116.

In an exemplary embodiment, the system 100 is supported by a rigid frame structure primarily composed of lightweight and durable aluminum extrusions, which provide an optimal strength-to-weight ratio, modularity, and ease of assembly, ensuring stability for the system components. However, the rigid frame structure is not limited to aluminum; alternative structural materials such as stainless steel for enhanced load-bearing capacity, polycarbonate or reinforced polymers for lightweight and corrosion resistance, and composite materials for improved vibration damping may also be employed depending on application requirements, environmental conditions, and cost considerations.

In an exemplary embodiment, the system 100 comprises a power supply unit 128. The power supply unit 128 provides regulated electrical power to all the system components. The power supply unit 128 ensures stable and uninterrupted operation, incorporating protection features such as overvoltage, overcurrent, and short-circuit safeguards. The power supply unit 128 may be, but not constricted to, one of: a switched-mode power supply (SMPS), a modular direct current (DC) power supply, and the like, depending on system requirements.

In an exemplary embodiment, the compute module housing 130 comprises, not limited to, one or more hardware processors, a memory unit, the plurality of controller units, and associated electronic circuitry. The compute module housing 130 is configured to provide structural support, electromagnetic shielding, and thermal management for reliable operation. The compute module housing 130 ensures secure housing of control electronics, protecting the control electronics from dust, vibration, and accidental contact. The compute module housing 130 serves as a central hub for executing control commands, coordinating subsystem operations, and managing the overall workflow of the system 100.

Figure 2:
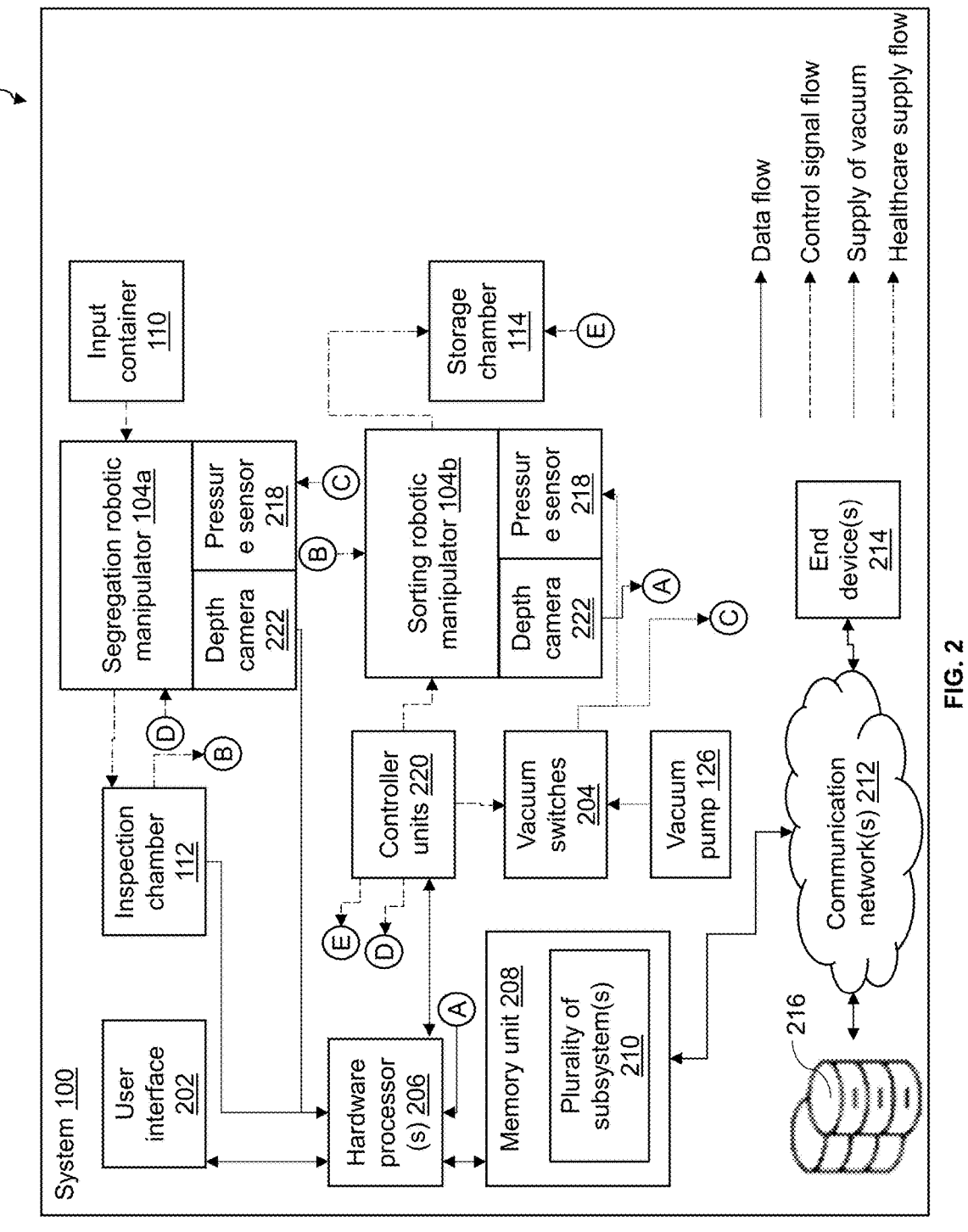
FIG. 2 illustrates an exemplary block diagram representation of a network architecture depicting the system for categorizing the unsegregated healthcare supplies into the predefined storage chambers using the healthcare supply metadata, in accordance with an embodiment of the present disclosure.

FIG. 2 illustrates an exemplary block diagram representation of a network architecture 200 depicting the system 100 for categorizing the unsegregated healthcare supplies into the predefined storage chambers 116 using the healthcare supply metadata, in accordance with an embodiment of the present disclosure.

According to an exemplary embodiment of the present disclosure, FIG. 2 depicts the network architecture 200 that includes the system 100. The system comprises one or more databases 216, the one or more hardware processors 206, and the one or more end devices 214. The one or more hardware processors 206, the one or more databases 216, and the one or more end devices 214 may be communicatively coupled via one or more communication networks 212, ensuring seamless data transmission, processing, and decision-making throughout a healthcare supply categorization workflow. The system 100 acts as a central processing unit within the network architecture 200, responsible for categorizing the unsegregated healthcare supplies into the predefined storage chambers 116 using the healthcare supply metadata. The system 100 is configured to execute a set of computer-readable instructions that control a plurality of subsystems 210, each configured for specific tasks such as data obtaining, manipulator control, metadata extraction, mapping, and categorization.

In an exemplary embodiment, the system 100 comprises the one or more hardware processors 206 and a memory unit 208. The memory unit 208 is operatively connected to the one or more hardware processors 206. The memory unit 208 comprises a set of computer-readable instructions in form of the plurality of subsystems 210, configured to be executed by the one or more hardware processors 206. The one or more hardware processors 206 may comprise a combination of discrete components, an integrated circuit, an application-specific integrated circuit, a field-programmable gate array, a digital signal processor, or other suitable hardware. The "software" may comprise one or more objects, agents, threads, lines of code, subroutines, separate software applications, two or more lines of code, or other suitable software structures operating in one or more software applications or the one or more hardware processors 206, that work cooperatively to control the one or more robotic manipulators 104, manage sensor data, and perform metadata-driven categorization tasks.

In an exemplary embodiment, the one or more hardware processors 206 may include, for example, microprocessors, microcomputers, microcontrollers, digital signal processors, central processing units, state machines, logic circuits, and/or any devices that manipulate data or signals based on operational instructions. Among other capabilities, the one or more hardware processors 206 may fetch and execute computer-readable instructions in the memory unit 208 operationally coupled with the system 100 for performing tasks such as running one or more AI models, processing the sensor data, motion planning, and/or any other functions. Any reference to a task in the present disclosure may refer to an operation or that may be performed by the plurality of subsystems 210, or associated components. The one or more hardware processors 206 are high-performance processors capable of real-time decision-making, ensuring synchronization of categorization activities with database records. The one or more hardware processors 206 may be, but not limited to, at least one of: multi-core central processing units (CPU), a graphics processing unit (GPU)-based processing unit, and the like that enhance an ability of the system 100 to categorize the unsegregated healthcare supplies into the predefined storage chambers 116.

In an exemplary embodiment, the one or more databases 216 may be configured to store and manage data related to various aspects of the system 100. The one or more databases 216 may store at least one of, but not limited to, storage chamber metadata, healthcare supply metadata, the user-defined sorting rules, historical sensor data, and the like. The one or more databases 216 serve as a centralized repository for critical data elements that are integral to the secure operation of the system 100, enabling efficient management and synchronization of data associated with the system 100. The one or more databases 216 enable the system 100 to dynamically retrieve, analyze, and update the stored data in real-time, for categorizing the unsegregated healthcare supplies into the predefined storage chambers 116 using the healthcare supply metadata. The one or more databases 216 may include different types of databases such as, but not limited to, relational databases (e.g., Structured Query Language (SQL) databases), non-Structured Query Language (NoSQL) databases (e.g., MongoDB, Cassandra), time-series databases (e.g., InfluxDB), and the like. The one or more databases 216 facilitate efficient storage, retrieval, and updating of data in real-time, ensuring that the system 100 is able to categorize the unsegregated healthcare supplies into the predefined storage chambers 116 using the healthcare supply metadata.

In an exemplary embodiment, the one or more end devices 214 are configured to enable a user of the one or more users to interact with the system 100 for controlling and monitoring the categorization of the unsegregated healthcare supplies. The one or more end devices 214 may be digital devices, computing devices, and/or networks. The one or more end devices 214 may include, but not limited to, a mobile device, a smartphone, a personal digital assistant (PDA), a tablet computer, a phablet computer, a wearable computing device, a virtual reality/augmented reality (VR/AR) device, a laptop, a desktop, and the like. The one or more end devices 214 are configured with the user interface 202 to enable seamless interaction between the user and the system 100. The user interface 202 may include graphical user interface (GUI) units, voice-based interfaces, and touch-based interfaces, depending on the capabilities of the system 100 being used. The GUI units may be configured to display outputs, including, but not restricted to, at least one of: system-related outputs, including, but not limited to: categorization outcomes, the healthcare supply metadata extracted from labels, chamber allocation status, expiry notifications, and error or retry logs. The one or more end devices 214 may also support multimodal inputs, allowing the user to interact through voice commands, text inputs, and gesture-based controls, ensuring accessibility and ease of use across different user demographics. This ensures accessibility and ease of use across diverse healthcare environments, including hospitals, pharmacies, and storage facilities. The one or more end devices 214 are configured to securely transmit and receive data to and from the system 100 via the one or more communication networks 212, ensuring real-time synchronization, secure metadata transfer, and uninterrupted categorization workflows.

In an exemplary embodiment, the system 100 is also configured with the user interface 202 (touch screen-based GUI) to enable seamless interaction between the user and the system 100. Through the user interface 202, the user may start and stop the system 100, monitor the status of ongoing sorting operations, and access diagnostic and troubleshooting information. The user interface 202 further enables retrieval of operational data, such as the number of healthcare supplies sorted, the categories, and alerts for handling expired and unrecognized healthcare supplies. This facilitates user-friendly management of the system 100 without requiring technical expertise.

In an exemplary embodiment, the one or more communication networks 212 may be, but not limited to, a wired communication network and/or a wireless communication network, a local area network (LAN), a wide area network (WAN), a Wireless Local Area Network (WLAN), a metropolitan area network (MAN), a telephone network, such as the Public Switched Telephone Network (PSTN) or a cellular network, an intranet, the Internet, a fiber optic network, a satellite network, a cloud computing network, a combination of networks, and the like. The wired communication network may comprise, but not limited to, at least one of: Ethernet connections, Fiber Optics, Power Line Communications (PLCs), Serial Communications, Coaxial Cables, Quantum Communication, Advanced Fiber Optics, Hybrid Networks, and the like. The wireless communication network may comprise, but not limited to, at least one of: wireless fidelity (wi-fi), cellular networks (including fourth generation (4G) technologies and fifth generation (5G) technologies), Bluetooth®, ZigBee®, long-range wide area network (LoRaWAN), satellite communication, radio frequency identification (RFID), 6G (sixth generation) networks, advanced IoT protocols, mesh networks, non-terrestrial networks (NTNs), near field communication (NFC), and the like, enabling flexibility in remote monitoring and control of healthcare supply categorization operations.

The one or more hardware processors 206 function as central computational units of the system 100, executing the one or more AI models, motion planning, and data processing workflows to analyze input data and generate high-level control commands. The plurality of controller units 220 acts as real-time interfaces between the one or more hardware processors 206 and electromechanical components. The plurality of controller units 220 receives the control commands from the one or more hardware processors 206 and translates the control commands into low-level actuation signals for other system components. Together, the one or more hardware processors 206 provide intelligence and decision-making, while the plurality of controller units 220 ensure precise execution of physical actions.

As shown in the network architecture 200, the user interface 202 enables bidirectional data flow with the one or more hardware processors 206, allowing the one or more users to provide commands and receive system feedback. The one or more hardware processors 206 exchange data with the user interface 202 and the plurality of controller units 220, executing the one or more AI models and processing the plurality of subsystems 210 to orchestrate the workflow. The plurality of controller units 220 exchange data with the one or more hardware processors 206 and generate control signals for the segregation robotic manipulator 104*a*, the sorting robotic manipulator 104*b*, and the vacuum switches 204.

The segregation robotic manipulator 104*a*, integrated with sensors, receives the control signals and data from the plurality of controller units 220, vacuum supply from the vacuum switches 204, and transfers the at least one healthcare supply from the input container 110 into the inspection chamber 112. The sensors include, but not limited to, a depth camera 222 associated with the segregation robotic manipulator 104*a* provides bidirectional data flow to support positioning and orientation, and a pressure sensor 218 associated with the segregation robotic manipulator 104*a* provides the pressure sensor data to verify gripping and releasing events.

A pressure sensor 218 associated with the segregation robotic manipulator 104*a* is configured to generate pressure sensor data used to verify gripping and releasing events of the healthcare supplies. In the context of this disclosure, the term pressure sensor 218 is used as a broad category that includes multiple sensing modalities, such as, without limitation, a force sensor, a pneumatic pressure sensor, and a vacuum pressure sensor, all of which can detect changes in applied pressure during manipulation. The force sensor is configured to detect the gripping force exerted by the one or more end-effectors 120 on the healthcare supply. The pneumatic pressure sensor is configured to measure air-pressure variations within pneumatic actuation lines to determine whether the one or more end-effectors 120 have successfully gripped/released the healthcare supply. The vacuum pressure sensor is configured to monitor suction pressure levels to confirm attachment/detachment of the healthcare supply when the suction-based gripper is used.

The sorting robotic manipulator 104*b*, integrated with the sensors, receives the control signals and data from the plurality of controller units 220, vacuum supply from the vacuum switches 204, and transfers the at least one healthcare supply from the inspection chamber 112 into the appropriate predefined storage chamber 116. The depth camera 222 associated with the sorting robotic manipulator 104*b* provides bidirectional data flow for precise localization during placement. The pressure sensor 218 in the sorting robotic manipulator 104*b* generates feedback data to verify successful handling.

The vacuum switches 204 receive control signals from the plurality of controller units 220, regulate vacuum supply from the vacuum pump 126, and distribute suction to the segregation robotic manipulator 104*a* and the sorting robotic manipulator 104*b*. The vacuum pump 126 supplies vacuum pressure to the vacuum switches 204, enabling the one or more end-effectors 120 of the segregation robotic manipulator 104*a* and the sorting robotic manipulator 104*b* to grip and release the at least one healthcare supply.

In an exemplary embodiment, the system 100 is implemented as a single integrated device. The implementation may rely on hardware, or on a hybrid of hardware and software, to execute the plurality of subsystems 210 responsible for metadata extraction, mapping, categorization, and robotic manipulation.

In some embodiments, the system 100 may further integrate with external or cloud-based servers to enhance processing speed and scalability. These external or cloud-based servers work in conjunction with the one or more hardware processors 206 by offloading computationally intensive tasks such as deep learning inference, large-scale metadata matching, and real-time database queries. The external or cloud-based servers may host high-performance GPUs, Tensor Processing Units (TPUs), or distributed computing clusters that accelerate processing of multi-perspective images, motion planning, and AI-driven classification. Data from the system 100 is securely transmitted to the external or cloud-based servers via the one or more communication networks 212, processed at high speed, and the results, such as target gripping points and storage chamber assignments, are transmitted back to the system 100 in real time, ensuring fast and efficient operation even with large volumes of the unsegregated healthcare supplies.

Though few components and the plurality of subsystems 210 are disclosed in FIG. 2, there may be additional components and subsystems which is not shown, such as, but not limited to, ports, routers, repeaters, firewall devices, network devices, the one or more databases 216, network attached storage devices, assets, machinery, instruments, facility equipment, emergency management devices, image capturing devices, any other devices, and combination thereof. The person skilled in the art should not be limiting the components/subsystems shown in FIG. 2. Although FIG. 2 illustrates the system 100, and the one or more end devices 214 connected to the one or more databases 216, one skilled in the art may envision that the system 100, and the one or more end devices 214 may be connected to several user devices located at various locations and several databases via the one or more communication networks 212.

Those of ordinary skilled in the art will appreciate that the hardware depicted in FIG. 2 may vary for particular implementations. For example, other peripheral devices such as an optical disk drive and the like, the LAN, the WAN, wireless (e.g., Wi-Fi) adapter, graphics adapter, disk controller, input/output (I/O) adapter also may be used in addition or place of the hardware depicted. The depicted example is provided for explanation only and is not meant to imply architectural limitations concerning the present disclosure.

Those skilled in the art will recognize that, for simplicity and clarity, the full structure and operation of all data processing systems suitable for use with the present disclosure are not being depicted or described herein. Instead, only so much of the system 100 as is unique to the present disclosure or necessary for an understanding of the present disclosure is depicted and described. The remainder of the construction and operation of the system 100 may conform to any of the various current implementations and practices that are known in the art.

Figure 3:
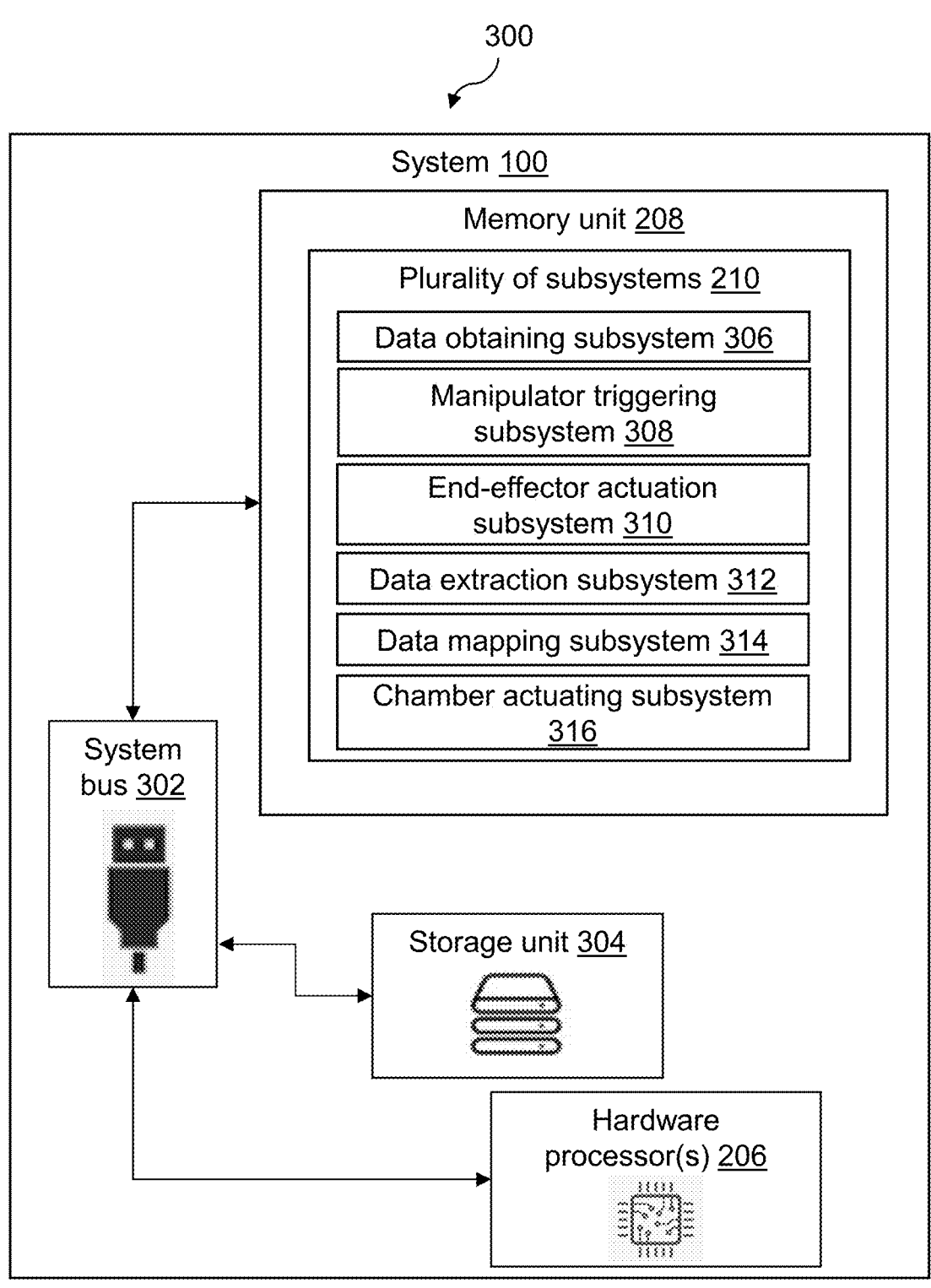
FIG. 3 illustrates an exemplary block diagram representation of the system as shown in FIG. 2 for categorizing the unsegregated healthcare supplies into the predefined storage chambers using the healthcare supply metadata, in accordance with an embodiment of the present disclosure.
Figure 4:
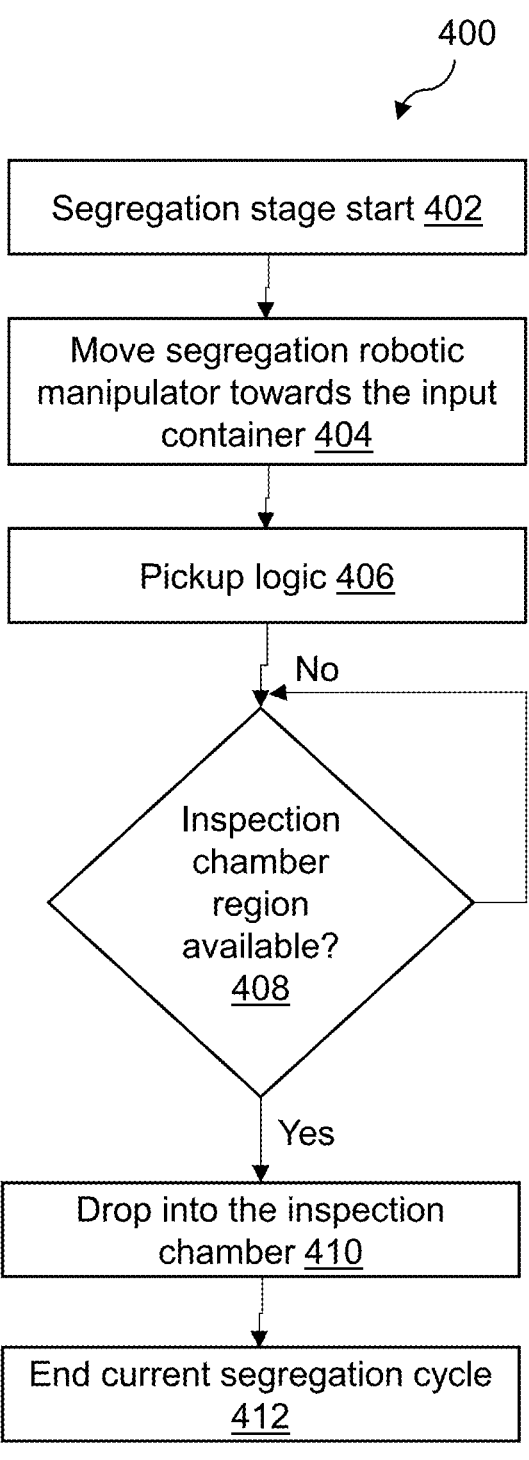
FIG. 4 illustrates an exemplary segregation flow diagram for gripping at least one healthcare supply from the unsegregated healthcare supplies in an input container, in accordance with an embodiment of the present disclosure.
Figure 5:
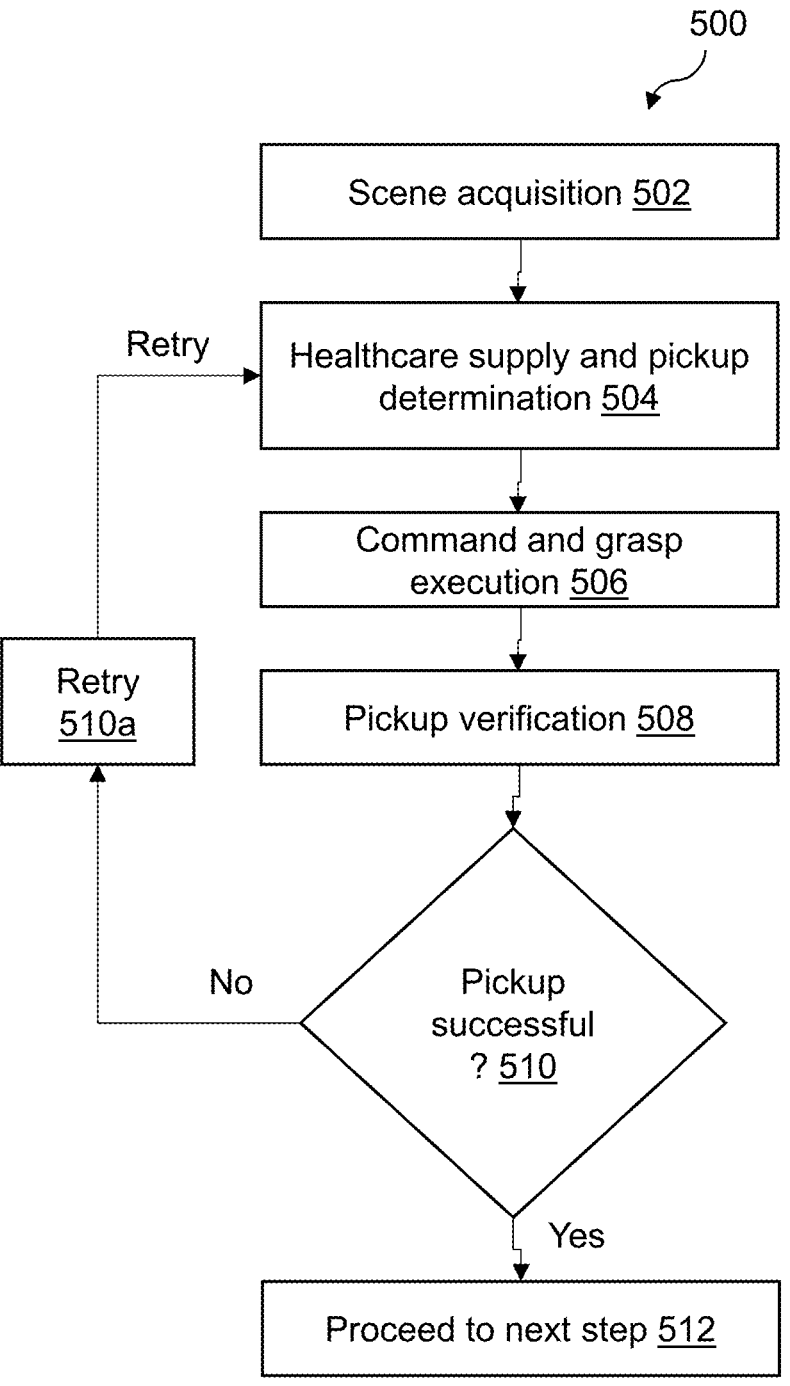
FIG. 5 illustrates an exemplary pickup logic flow diagram for gripping the at least one healthcare supply from the unsegregated healthcare supplies in the input container, in accordance with an embodiment of the present disclosure.
Figure 6:
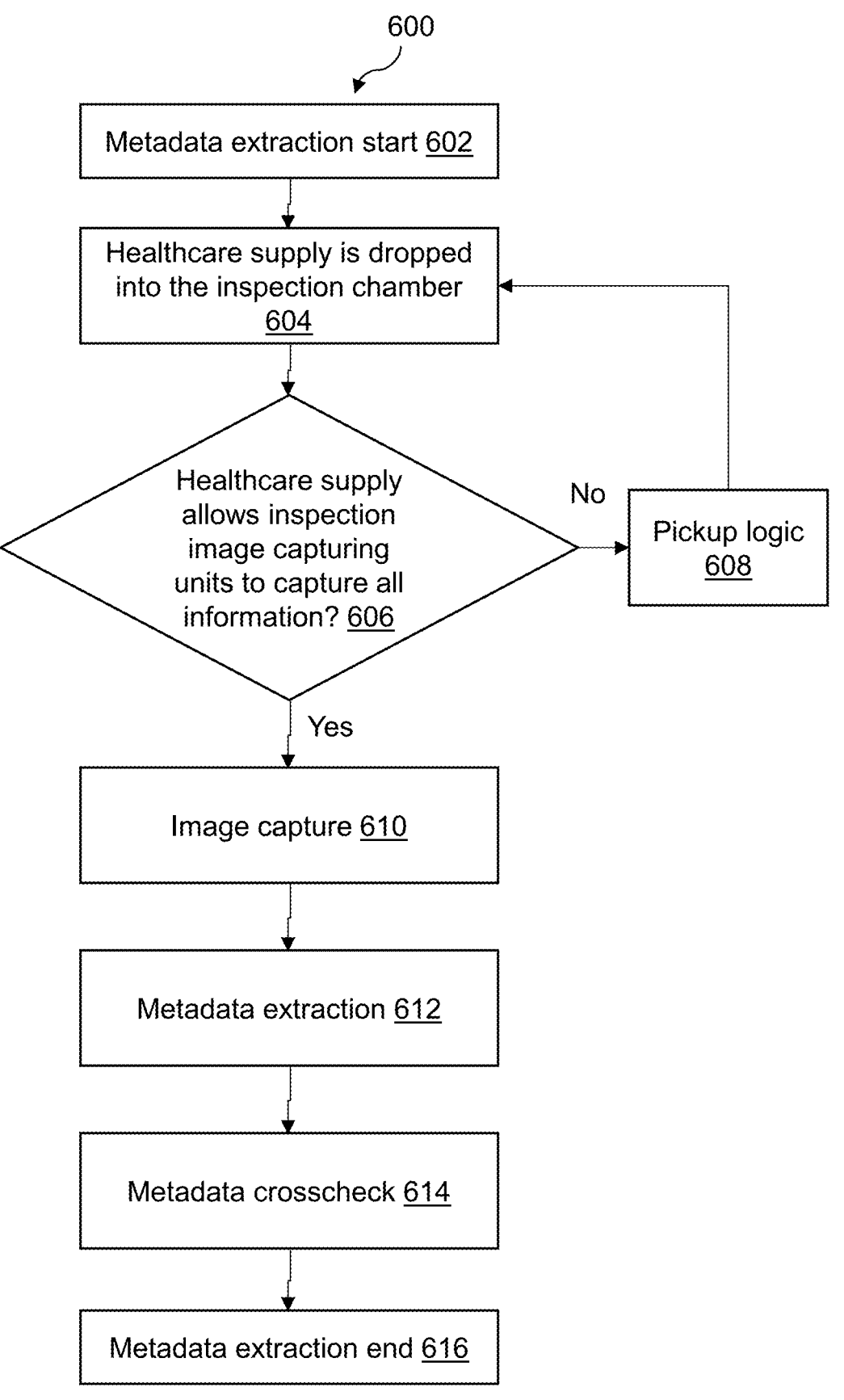
FIG. 6 illustrates an exemplary data extraction flow diagram for extracting the healthcare supply metadata from the at least one healthcare supply, in accordance with an embodiment of the present disclosure.
Figure 7:
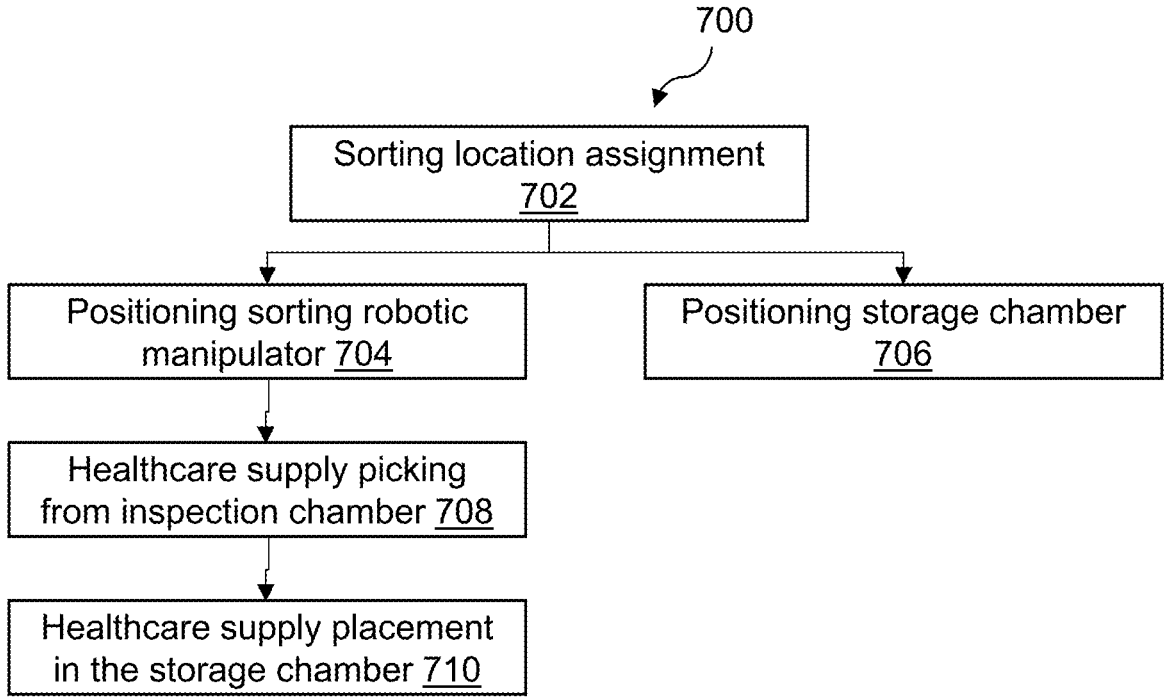
FIG. 7 illustrates an exemplary sorting flow diagram for releasing the at least one healthcare supply into the predefined storage chambers to categorize the unsegregated healthcare supplies, in accordance with an embodiment of the present disclosure.

FIG. 3 illustrates an exemplary block diagram representation 300 of the system 100 as shown in FIG. 2 for categorizing the unsegregated healthcare supplies into the predefined storage chambers 116 using the healthcare supply metadata, in accordance with an embodiment of the present disclosure;

FIG. 4 illustrates an exemplary segregation flow diagram 400 for gripping the at least one healthcare supply from the unsegregated healthcare supplies in the input container 110, in accordance with an embodiment of the present disclosure;

FIG. 5 illustrates an exemplary pickup logic flow diagram 500 for gripping the at least one healthcare supply from the unsegregated healthcare supplies in the input container 110, in accordance with an embodiment of the present disclosure;

FIG. 6 illustrates an exemplary data extraction flow diagram 600 for extracting the healthcare supply metadata from the at least one healthcare supply, in accordance with an embodiment of the present disclosure; and FIG. 7 illustrates an exemplary sorting flow diagram 700 for releasing the at least one healthcare supply into the predefined storage chambers 116 to categorize the unsegregated healthcare supplies, in accordance with an embodiment of the present disclosure.

In an exemplary embodiment, the system 100 comprises the one or more hardware processors 206, the memory unit 208, and a storage unit 304. The one or more hardware processors 206, the memory unit 208, and the storage unit 304 are communicatively coupled through a system bus 302 or any similar mechanism. The system bus 302 functions as the central conduit for data transfer and communication between the one or more hardware processors 206, the memory unit 208, and the storage unit 304. The system bus 302 facilitates the efficient exchange of information and instructions, enabling the coordinated operation of the system 100. The system bus 302 may be implemented using various technologies including, but not limited to, parallel buses, serial buses, and high-speed data transfer interfaces such as, but not limited to, at least one of a: universal serial bus (USB), peripheral component interconnect express (PCIe), and similar standards.

In an exemplary embodiment, the memory unit 208 is operatively connected to the one or more hardware processors 206. The memory unit 208 comprises the plurality of subsystems 210 in the form of programmable instructions executable by the one or more hardware processors 206. The plurality of subsystems 210 comprises, but not limited to: a data obtaining subsystem 306 configured to obtain positional data, image data, and sensor signals; a manipulator triggering subsystem 308 configured to generate the control commands; an end-effector actuation subsystem 310 configured to process the pressure sensor data; a data extraction subsystem 312 configured with the one or more AI models to extract the healthcare supply metadata; a data mapping subsystem 314 configured to map the healthcare supply metadata against the storage chamber metadata; and a chamber actuating subsystem 316 configured to operate a chamber positioning mechanism 118 for storage chamber actuation. The one or more hardware processors 206, as used herein, means any type of computational circuit, such as, but not limited to, the microprocessor unit, microcontroller, complex instruction set computing microprocessor unit, reduced instruction set computing microprocessor unit, very long instruction word microprocessor unit, explicitly parallel instruction computing microprocessor unit, graphics processing unit, digital signal processing unit, or any other type of processing circuit. The one or more hardware processors 206 may also include embedded controllers, such as generic or programmable logic devices or arrays, application-specific integrated circuits, single-chip computers, and the like.

The memory unit 208 may be the non-transitory volatile memory and the non-volatile memory. The memory unit 208 may be coupled to communicate with the one or more hardware processors 206, such as being a computer-readable storage medium. The one or more hardware processors 206 may execute machine-readable instructions and/or source code stored in the memory unit 208. A variety of machine-readable instructions may be stored in and accessed from the memory unit 208. The memory unit 208 may include any suitable elements for storing data and machine-readable instructions, such as read-only memory, random access memory, erasable programmable read-only memory, electrically erasable programmable read-only memory, a hard drive, a removable media drive for handling compact disks, digital video disks, diskettes, magnetic tape cartridges, memory cards, and the like. In the present embodiment, the plurality of subsystems 210 is stored in the memory unit 208 as executable instructions, ensuring seamless integration with the one or more hardware processors 206 for categorization workflows.

The storage unit 304 may be a cloud storage or the one or more databases 216 such as those shown in FIG. 2. The storage unit 304 may store, but not limited to, recommended course of action sequences dynamically generated by the system 100. The action sequences comprise obtaining the positional data from the one or more robotic manipulators 104, receiving and processing the multi-perspective healthcare supply images, performing metadata extraction through the one or more AI models, executing metadata-to-storage chamber mapping, and generating actuator commands for robotic manipulator movement, and the like. The storage unit 304 retain historical operational data such as previous gripping attempts, orientation adjustment cycles, metadata extraction outcomes, and mapping correlation. The storage unit 304 supports real-time synchronization with the plurality of subsystems 210 and ensures that the recommendations and action sequences remain accurate and up-to-date. Additionally, the storage unit 304 may retain previous action sequences for comparison and future reference, enabling continuous refinement of the system 100 over time. The storage unit 304 may be any kind of database such as, but not limited to, relational databases, dedicated databases, dynamic databases, monetized databases, scalable databases, cloud databases, distributed databases, any other databases, and a combination thereof.

Furthermore, the storage unit 304 and the one or more databases 216 may integrate with, but not limited to, at least one of: external data repositories, including but not limited to: manufacturer databases, medicine reference databases, barcode/QR code repositories, expiry-date validation registries, regulatory compliance databases, and hospital inventory systems. These integrations ensure that the storage unit 304 and the one or more databases 216 remain central repositories for managing critical data required by the system 100, enabling dynamic real-time updates, seamless metadata validation, and actionable insights for healthcare supply categorization. This interconnected architecture supports adaptability, scalability, and ensures that the system 100 can deliver reliable, accurate, and secure categorization of the healthcare supplies.

In an exemplary embodiment, the data obtaining subsystem 306 is configured to obtain the positional data (numerical representations of spatial coordinates and orientation) associated with the one or more robotic manipulators 104 and the predefined storage chambers 116. The data obtaining subsystem 306 is configured to obtain the positional data, the color data and the depth data, the multi-perspective healthcare supply images and the orientation data, the storage chamber metadata, and the pressure sensor data.

The positional data is obtained one or more of:

a) encoder feedback signals, generated by the encoders operatively associated with the one or more actuators 106. The encoders are electromechanical devices that convert rotary and linear motion into electrical signals, thereby providing high-resolution position and velocity feedback. For example, a rotary encoder attached to the servo motor may output quadrature pulses that track the angular displacement of the one or more robotic manipulators 104, b) limit switch signals, which define reference positions (home or boundary positions) of the one or more robotic manipulators 104 and the chamber positioning mechanism 118. The limit switch signals ensure safe and repeatable mechanical positioning by signaling when a physical travel limit has been reached, c) step count data generated by actuator drives of the one or more actuators 106 (stepper motors or other digital actuators). The step count data provides incremental motion feedback based on commanded step pulses, enabling open-loop and hybrid closed-loop control of manipulator positioning, and d) the depth data captured by the one or more manipulator image capturing units 122 provides 3D point cloud data of the input container environment. The depth data supplements mechanical sensor data by allowing detection of object position and height in cluttered environments.

The color data and the depth data are obtained from the one or more manipulator image capturing units 122. The color data and the depth data are visual spectral information and spatial depth information used for healthcare supply recognition, segmentation, and manipulator alignment. The depth data and the color data are captured by a segregation vision image capturing unit 122a and a sorting vision image capturing unit 122b, associated with the one or more manipulator image capturing units 122. The segregation vision image capturing unit 122a, positioned to view the input container 110, provides 3D scene information and RGB imagery to enable accurate localization and pickup of the at least one healthcare supply. The sorting vision image capturing unit 122b, oriented toward the inspection chamber 112, captures visual and depth information to support precise metadata extraction and orientation analysis of the at least one healthcare supply. For example, the color data may detect the label region, while the depth data ensures accurate gripper approach trajectories.

The multi-perspective healthcare supply images and the orientation data are obtained from the one or more inspection image capturing units 124, which provide comprehensive visual information of the healthcare supply's packaging, label placement, and angular alignment.

The storage chamber metadata is associated with the plurality of storage chambers 116, defined as pre-assigned descriptive information mapped to the unique chamber identifiers. The pressure sensor data associated with the one or more end-effectors 120 obtained from the pressure sensor 218 is defined as force and vacuum level measurements indicating gripping and release success. For example, in the suction-based gripper, the pressure sensors 218 provide vacuum feedback to verify the successful pick-up of the blister packs and bottles.

In an exemplary embodiment, the manipulator triggering subsystem 308 is configured to generate the control command (as a set of electrical or digital signals) that is transmitted to the one or more actuators 106 to achieve a desired manipulator movement. The manipulator triggering subsystem 308 ensures that the one or more robotic manipulators 104 reach, grip, and release the at least one healthcare supply with precision by processing the positional data, the color data, and the depth data.

The manipulator triggering subsystem 308 is further configured to process the positional data using a mathematical representation model to determine a current location of the one or more robotic manipulators 104. The mathematical representation model represents the geometry and motion of the one or more robotic manipulators 104. The mathematical representation model translates actuator measurements (e.g., encoder counts or step counts from the stepper motors) into spatial positions and orientations in a Cartesian workspace. For example, a Denavit-Hartenberg (DH) parameter model is a standardized method in robotics to represent manipulator geometry using four parameters (link length, link twist, joint angle, and link offset). Each joint of the manipulator is expressed as a homogeneous transformation matrix based on these parameters. By multiplying the series of transformation matrices corresponding to successive joints, the DH parameter model computes the precise location and orientation of the one or more end-effectors 120 in 3D space. In the present system, the one or more hardware processors 206 executes this model in real-time, continuously updating the end-effector pose based on incoming encoder feedback and actuator commands, thereby enabling accurate motion planning, collision avoidance, and gripping of the healthcare supplies.

For example, a forward kinematics model is the mathematical representation model used to determine the position and orientation of one or more robotic manipulators 104 given a set of joint values. The forward kinematics model computes the position and orientation of the one or more end-effectors 120 based on known joint variables (angles, displacements). The forward kinematics model translates joint encoder readings into Cartesian workspace positions for accurate gripping and releasing. Knowing a base rotation is 45° and arm extension is 20 cm, the forward kinematics model outputs the location in Cartesian coordinates.

For example, an inverse kinematics solver is the mathematical representation model used in robotics and computer animation to determine the joint parameters (like angles or displacements) required to place the one or more end-effectors 120 at a specific desired position and orientation. The inverse kinematics solver computes the necessary joint variables to place the one or more end-effectors 120 at a desired position and orientation. The inverse kinematics solver converts the target location (e.g., "pick the at least one healthcare supply at X=10, Y=5, Z=3") into actuator commands for each manipulator joint. To reach a pill bottle at a specific point, the inverse kinematics solver determines how much each actuator 106 (shoulder, elbow, wrist) must rotate.

For instance, a Jacobian model is a mathematical matrix relating joint velocities of the one or more robotic manipulators 104 to the linear and angular velocities of the one or more end-effectors 120. The Jacobian matrix is computed from the current joint positions using parameters such as link lengths, link twists, and offsets obtained from the Denavit-Hartenberg (DH) model. The one or more hardware processors 206 execute this Jacobian model in real time using the encoder feedback signals from the actuators, thereby enabling dynamic control of speed, force, and stability during motion. For example, when gripping a fragile vial, the Jacobian model allows the system to regulate actuator velocities and distribute forces evenly across the manipulator joints, ensuring smooth placement without causing damage.

The manipulator triggering subsystem 308 is further configured to process the color data and the depth data using a vision-based object detection model associated with the one or more AI models to determine the target location of the at least one healthcare supply within the input container 110. The vision-based object detection model is a computer vision model that's trained to find and categorize specific objects within images or videos. The vision-based object detection model goes beyond simply identifying what an image is (e.g., "a picture of a cat") by also telling you where each object is located (e.g., "a cat is in this specific box"). The vision-based object detection model identifies and localizes the at least one healthcare supply within captured images. The vision-based object detection model detects the at least one healthcare supply and provides a bounding box and pixel coordinates for further processing. The vision-based object detection model generates the bounding box, which is a rectangular region enclosing the detected healthcare supply. Along with the bounding box, the vision-based object detection model outputs the pixel coordinates (x, y positions of the corners or center of the box) that define at least healthcare supply's precise location in the image frame. The pixel coordinates are then used by the system 100 to guide the one or more robotic manipulators 104 toward the detected at least one healthcare supply for gripping and processing. For instance, the vision-based object detection model detects the blister pack of tablets within the input container 110.

The target location is calculated 3D coordinates in the input container 110 where the at least one healthcare supply is located. The target location serves as the end-point for the planned manipulator movement. For instance, the blister pack is determined to be at coordinates (x=100 millimeters (mm), y=40 mm, z=70 mm).

The manipulator triggering subsystem 308 is further configured to generate the control command by computing a motion trajectory, which is time-parameterized path in the 3D space that specifies how the one or more robotic manipulators 104 move from the current location to the target location. The motion trajectory is generated using a motion planning model associated with the one or more AI models. The motion planning model is a computational framework used in robotics and computer science to find a sequence of valid configurations that moves the one or more robotic manipulators 104 or object from a starting point to a destination. The goal is to compute a continuous path that avoids collisions with known obstacles while adhering to kinematic and dynamic constraints of the one or more robotic manipulators 104. For instance, the motion trajectory may be computed such that the mechanical gripper moves downward, advances forward, and applies a slight rotational adjustment to prevent collision with adjacent healthcare supplies. The motion planning model converts the high-level control commands into feasible paths, considering constraints such as joint limits collision avoidance, and task-specific requirements. The motion planning model comprises, but not constricted to, at least one of: the inverse kinematics solver, a trajectory optimization model, a reinforcement learning-based motion policy, and the like.

The inverse kinematics solver calculates the joint variables required to position the one or more end-effectors 120 at a desired Cartesian coordinate in the workspace. The inverse kinematics solver maps the target location into actuator-specific commands, enabling direct control of the manipulators. For example, for reaching (x=100 mm, y=40 mm, z=70 mm), the inverse kinematics solver computes joint rotations $\theta_1=45°$, $\theta_2=30°$, $\theta_3=-15°$.

The trajectory optimization model computes the optimal motion trajectory based on defined optimization criteria, using numerical optimization techniques to refine candidate paths. The trajectory optimization model minimizes cost functions such as travel time, jerk, actuator torque, and energy usage while ensuring safe motion under system constraints. For example, the manipulator path is optimized to minimize actuator torque while avoiding collision with a tall medicine bottle located nearby.

The reinforcement learning-based motion policy is a machine learning framework trained through trial and error in simulated and real environments to perform motion tasks. The reinforcement learning-based motion policy generates adaptive movement strategies in unpredictable and dynamic settings by learning to maximize task success while minimizing failures. For instance, the reinforcement learning-based motion policy learns to adjust the path if the healthcare supply shifts position in the input container 110.

In an exemplary embodiment, the end-effector actuation subsystem 310 is configured to operate the one or more end-effectors 120 based on the pressure sensor data to ensure reliable gripping and releasing of the at least one healthcare supply. The pressure sensor data refers to real-time measurements obtained from the pressure sensors 218 one of: embedded in and associated with the one or more end-effectors 120, indicating one of: vacuum levels (for suction-based grippers) and gripping force (for mechanical grippers). The end-effector actuation subsystem 310 is further configured to process the pressure sensor data by one of: monitoring vacuum levels in the suction-based gripper and gripping force in the mechanical gripper: The end-effector actuation subsystem 310 determines whether the at least one healthcare supply has been securely gripped or successfully released. For example, a vacuum sensor detects −45 Kilopascal (kPa) inside a suction cup, confirming attachment to the medicine blister pack. A force sensor registers 2.5 Newtons between gripper fingers, confirming a secure grasp of a pill bottle.

In alternative exemplary embodiments, the system 100 may further include a variety of sensors depending on the operational requirements. The vacuum sensor measures the negative pressure level in the suction-based gripper to confirm whether suction has been successfully established during gripping. The force sensor detects the gripping force applied by the mechanical gripper to ensure the gripping force is within safe limits, preventing both slippage and damage to fragile healthcare supplies.

Additional sensors may be operatively integrated with the system 100 to enhance accuracy, safety, and reliability during operation. A proximity sensor is configured to detect nearby objects or obstacles within the workspace, thereby supporting collision avoidance by generating alerts or corrective signals when the robotic manipulators 104 approach restricted zones. A temperature sensor is configured to monitor thermal conditions of critical components such as actuators, vacuum pumps, and controllers, thereby ensuring system safety during extended operation by preventing overheating. An inertial measurement unit (IMU), which combines accelerometers and gyroscopes, is configured to track the motion dynamics of the one or more robotic manipulators 104, including acceleration, angular velocity, and orientation, thereby improving motion stability and feedback control. For example, a proximity sensor may prevent a manipulator from colliding with the frame, a temperature sensor may trigger a cooling mechanism when the vacuum pump exceeds a threshold temperature, and an IMU may provide real-time orientation feedback for smoother end-effector placement.

The end-effector actuation subsystem 310 is configured to compare the monitored one of: the vacuum levels in the suction-based gripper and the gripping force in the mechanical gripper against predefined threshold values to verify successful gripping and releasing of the at least one healthcare supply. The predefined threshold values are numerical limits of pressure and force that distinguish between a valid grip/release and an unsuccessful attempt. If the monitored values meet or exceed the predefined threshold values, the grip/release is considered successful; otherwise, corrective action is triggered. For instance, the suction-based gripper may require at least −30 kPa vacuum to validate a grip, whereas the mechanical gripper may require at least 2 Newton gripping force to confirm adequate holding of the healthcare supply.

The predefined threshold values are generated based on historical pressure sensor data associated with the gripping of the unsegregated healthcare supplies. The historical pressure sensor data refers to previously collected records of pressure and force measurements during prior gripping and releasing operations. The historical pressure sensor data is analyzed to generate adaptive, predefined threshold values, ensuring the system 100 may adjust for variations in packaging material, supply weight, and surface texture. For example, if the historical pressure sensor data shows that the blister packs require an average vacuum of −35 kPa, the system 100 may set the predefined threshold value at −30 kPa to account for operational variability. If the suction cup only reaches −10 kPa instead of −30 kPa, the system 100 recognizes an incomplete grip and initiates the corrective actions.

In one technical enhancement, the end-effector actuation subsystem 310 may incorporate a scoring mechanism to evaluate grip quality beyond a simple pass/fail determination. The scoring mechanism assigns a numerical score, for example on a scale of 0-100, to each gripping attempt. The numerical score is computed using a weighted combination of sensor-derived parameters such as a vacuum/force ratio, a stability index, and a historical similarity index. The vacuum/force ratio is calculated by dividing the achieved vacuum level or gripping force by the threshold value, thereby normalizing the current measurement against an optimal reference. The stability index measures short-term variation in sensor readings, such as pressure fluctuations over a 200-millisecond window, where lower variance corresponds to higher stability. The historical similarity index evaluates how closely the current gripping pattern matches successful grip profiles stored in historical datasets, using statistical correlation or machine learning classifiers. Tunable weights are assigned to each parameter, and the resulting weighted sum determines the grip quality score. Higher scores reflect stronger and more reliable grips, whereas lower scores indicate weak or unstable attempts. For example, a suction-based grip achieving −32 kPa against a threshold of −30 kPa with low variance may yield a score of 90, while an attempt with only −12 kPa and high fluctuation may yield a score of 25. The computed numerical score is then used to guide corrective actions, wherein grips scoring above 80 are accepted, grips between 50 and 79 trigger a re-grasp sequence, and grips below 50 initiate a repositioning sequence before retry.

The end-effector actuation subsystem 310 is further configured to modify the control command to initiate one of: the re-grasp sequence and the repositioning sequence (corrective action). The re-grasp sequence is defined as a corrective maneuver wherein the one or more robotic manipulators 104 attempt to reapply the gripping action to the same healthcare supply without altering the initial alignment and orientation. The repositioning sequence is defined as an adjustment maneuver wherein the one or more robotic manipulators 104 alter the position, angle, and orientation of the one or more end-effectors 120 relative to the healthcare supply before reattempting the gripping action. Both re-grasp and repositioning sequences improve the operational reliability of the system 100 by compensating for failed, incomplete, and partial gripping attempts. These corrective actions reduce the risk of supply misclassification, damage, and failed transfers during the categorization process.

This initiation is based on: a) the pressure sensor data indicating one of: an ineffective gripping and releasing, and b) comparative analysis between one of: the vacuum levels and the gripping force against the predefined threshold values. For instance, the suction-based gripper reattempts to pick up the blister pack of tablets after the vacuum sensor detects only −10 kPa, which is below the required threshold value of −30 kPa, indicating insufficient suction. The mechanical gripper adjusts the alignment by shifting laterally 5 mm to center itself around a cylindrical pill bottle after the force sensor detects uneven pressure distribution below the predefined threshold value. Based on such discrepancies, the end-effector actuation subsystem 310 modifies the control command to trigger one of: the re-grasp sequence and the repositioning sequence, ensuring corrective handling of the at least one healthcare supply.

As shown in FIG. 4, at step 402, the segregation is initiated to isolate at least one healthcare supply from the unsegregated healthcare supplies contained in the input container 110. This stage prepares the at least one healthcare supply for transfer to the inspection chamber 112 for downstream processing. At step 404, the system 100 transmits a motion command to the segregation robotic manipulator 104a. The segregation robotic manipulator 104a moves to a specific region within the input container 110. Functionally, this ensures the segregation robotic manipulator 104a is positioned correctly for initiating gripping. At step 406, once the segregation robotic manipulator 104a is positioned at the target location, the pickup logic is executed. The pickup logic refers to a predefined control sequence where the segregation robotic manipulator 104a actuates the one or more end-effectors 120 (illustratively implemented as a vacuum suction cup) to grip the at least one healthcare supply. At step 408, after a successful pickup, the system 100 checks whether the inspection chamber region is available for depositing the at least one healthcare supply. This involves monitoring the real-time position of the sorting robotic manipulator 104b to ensure the sorting robotic manipulator 104b is not occupying the inspection chamber region. The check prevents collisions between the segregation robotic manipulator 104a and the sorting robotic manipulator 104b, thus ensuring safe and synchronized operation. If the inspection chamber 112 is not available, the segregation robotic manipulator 104a waits in a holding state until the inspection chamber region becomes free.

At step 410, when the inspection chamber 112 is available, the system 100 issues the control command to the segregation robotic manipulator 104a to release the gripped at least one healthcare supply. The one or more end-effectors 120 execute a controlled release, allowing the at least one healthcare supply to be placed in the inspection chamber 112 in a defined orientation. At step 412, following successful release into the inspection chamber 112, the segregation robotic manipulator 104a returns to the ready position, awaiting the next cycle. This marks the end of the segregation stage for the current at least one healthcare supply.

As shown in FIG. 5, upon reaching the desired location within the input container 110, the pickup logic initiates scene acquisition at step 502. The scene acquisition is the process of capturing visual and spatial data. At step 504, from the acquired scene data, the system 100 identifies the at least one healthcare supply. The system 100 then selects the optimal pickup point, which maximizes the likelihood of a successful grip. In this step 506, the system 100 issues the motion command to the one or more robotic manipulators 104 to move toward the selected pickup point. Once aligned, the one or more end-effectors 120 are actuated to perform the gripping action.

At step 508, pickup verification is executed, which is the process of confirming whether the gripping action was successful. At step 510, the system 100 evaluates the pickup verification results. If the pickup is deemed successful, the one or more robotic manipulators 104 proceed to the next step in the workflow. At step 512, when pickup is successful, the one or more robotic manipulators 104 continue with the downstream process, moving the at least one healthcare supply toward the inspection chamber 112. At step 510a, if pickup is unsuccessful, the system 100 initiates a retry cycle. The retry cycle refers to a corrective control strategy in which the one or more robotic manipulators 104 one of: adjust the pickup location for the same healthcare supply and select an alternate healthcare supply. The retry cycle continues until the successful pickup is achieved.

In an exemplary embodiment, the data extraction subsystem 312 is configured with the one or more AI models to process the multi-perspective healthcare supply images for extracting the healthcare supply metadata. The one or more AI models may comprise, but not restricted to, at least one of: an image segmentation model, an object detection model (e.g., You Only Look Once (YOLO)), an optical character recognition (OCR) model, a barcode or QR code recognition model, a vision-language model (e.g., Contrastive Language-Image Pre-training (CLIP)), and the like.

The image segmentation model is a computer vision model that partitions an image into distinct regions or objects at the pixel level. Instead of just drawing a box around an object like in object detection, it creates a "mask" that precisely outlines the shape of the object, assigning every pixel a label. At its core, an image segmentation model is a dense prediction model. It takes an image as input and outputs a pixel-by-pixel map, often the same size as the input image. Each pixel in this output map is assigned a category label, effectively creating a segmented image. This is typically achieved using a type of neural network called a Fully Convolutional Network (FCN) or a similar encoder-decoder architecture. This encoder learns and compresses the image features, while the decoder upsamples those features to produce the final, high-resolution segmentation map.

The image segmentation model partitions the multi-perspective healthcare supply image into multiple segments, each representing distinct regions. The image segmentation model isolates the label region from nearby packaging information, graphics, and background, ensuring accurate metadata extraction. The image segmentation model isolates the label region from surrounding packaging elements, graphics, and background by assigning a class label to each pixel in the captured image. By separating the pixels belonging to the label from those of logos, decorative elements, and irrelevant background, the image segmentation model produces a clean mask of the label region. The clean mask ensures that subsequent OCR and barcode recognition processes analyze only the relevant textual and symbolic data, thereby improving accuracy and reducing false detections. For instance, the image segmentation model separates the white printed label of a syrup bottle from the colorful packaging to allow clear reading of dosage details.

The image segmentation model is trained using a pixel-level annotated dataset, where each pixel of the multi-perspective healthcare supply images is labeled according to the corresponding class (e.g., label text region, packaging, background). During training, the image segmentation model learns to assign each pixel a probability distribution over possible classes. The training process minimizes a segmentation loss function, commonly a combination of a cross-entropy loss and a Dice coefficient loss (or Intersection over Union), ensuring accuracy in both global structure and fine edges. Data augmentation (rotations, brightness adjustments, random crops) is applied to handle real-world variations in orientation and lighting. The result is a trained image segmentation model capable of partitioning unseen images into distinct, meaningful regions, ensuring precise isolation of the label regions from packaging and background during metadata extraction.

The object detection model is a type of computer vision model that's trained to identify and locate specific objects within images or videos. Unlike simple image classification the object detection model tells you what an entire image contains, object detection provides the bounding box around each object, indicating its precise location, and a class label, telling you what the object is. The object detection model is an AI framework trained to locate and identify specific alphanumeric text within the label regions of interest on the at least one healthcare supply. The object detection model localizes the alphanumeric text on the at least one healthcare supply by drawing the bounding boxes, thereby focusing the extraction process. The object detection model identifies areas of interest where textual and symbolic information is likely present. The object detection model then generates the bounding boxes with the pixel coordinates around the alphanumeric text, effectively isolating the alphanumeric text from the rest of the packaging. For instance, the object detection model highlights the rectangular label area containing the alphanumeric text on a pill bottle, isolating the rectangular label from the rest of the packaging for OCR analysis.

The object detection model is trained using a supervised machine learning pipeline, where a large dataset of healthcare supply images is annotated with the bounding boxes and class labels indicating the precise location of the alphanumeric text. During training, the object detection model learns to minimize a combined loss function that includes classification loss (e.g., cross-entropy for correct label identification) and localization loss (e.g., regression loss such as Smooth L1 for bounding box coordinates). The trained object detection model outputs the bounding boxes with confidence scores, enabling precise localization of the alphanumeric text on the at least one healthcare supply in real-time. In another exemplary embodiment, the object detection model is trained using deep neural architectures such as the YOLO (You Only Look Once) or Faster Region-based Convolutional Neural Network (R-CNN). The training dataset comprises annotated healthcare supply images with the bounding boxes highlighting the label areas containing the alphanumeric text. The object detection model learns to detect rectangular regions of interest (ROIs) where metadata such as medicine name, dosage, and expiry date are printed. This trained capability allows the system 100 to automatically focus on the relevant regions for metadata extraction, thereby improving accuracy and efficiency.

The OCR model is a computer vision and machine learning model that converts images of text into machine-readable text. The OCR model allows a computer to "read" text from a photo, scanned document, or Portable Document Format (PDF) file, and then process or edit that text. The OCR model is configured to extract and convert the alphanumeric text in the multi-perspective healthcare supply images into machine-readable characters. The OCR model scans printed and embossed characters on the label areas to extract the healthcare supply metadata. The OCR model segments the multi-perspective healthcare supply image into character regions, converts pixel patterns into feature vectors, and maps the feature vectors to corresponding alphanumeric characters. Both the printed text (e.g., medicine names, dosage, expiry dates) and the embossed characters (e.g., batch codes pressed into blister packs) are recognized. For example, the OCR model converts the printed alphanumeric text "Ibuprofen 400 mg, Exp: 07/2027" from the multi-perspective healthcare supply image of a tablet strip into structured digital data.

The OCR model is trained using a large dataset of labeled text images, where each input image corresponds to a ground-truth transcription of the characters. Training begins with preprocessing, such as grayscale conversion, normalization, and noise reduction, to enhance text visibility. Each character (or sequence of characters) is predicted using a Connectionist Temporal Classification (CTC) loss function, which aligns the predicted sequence with the ground-truth transcription without requiring explicit segmentation of characters.

The OCR model is exposed to diverse fonts, sizes, orientations, and languages during training, with data augmentation techniques (rotation, blur, occlusion, lighting variations) applied to mimic real-world conditions such as tilted labels and low lighting. Over time, the OCR model learns robust mappings from pixel patterns to alphanumeric outputs. The trained OCR model may then take the multi-perspective healthcare supply images as input and reliably output machine-readable characters representing medicine names, dosages, batch numbers, and expiry dates.

The barcode or QR code recognition model is a computer vision algorithm that's specifically trained to detect and decode these types of optical machine-readable representations of data. The barcode or QR code recognition model decodes machine-readable identifiers embedded in barcodes or QR codes. The barcode or QR code recognition model extracts numeric and alphanumeric strings directly encoded in the label for traceability, authentication, and categorization. The barcode or QR code recognition model detects and decodes machine-readable patterns such as linear barcodes and two-dimensional QR codes printed on the healthcare supply label. The barcode or QR code recognition model extracts the encoded numeric and alphanumeric strings. The numeric and alphanumeric strings represent lot numbers, product identities, or manufacturer details that are critical for traceability, authentication, and categorization. The recognition process is robust to varying lighting conditions, partial occlusion, and distortions on curved surfaces. For example, the QR code on a blister strip decodes to "MFR-12345, LOT-56789, EXP-2026".

The vision-language model is an advanced AI model capable of jointly processing visual features (e.g., images) and textual features (e.g., printed words) to derive contextual meaning. The vision-language model interprets the healthcare supply metadata by combining image cues (brand logos, label layouts) with textual content, allowing robust metadata extraction even in low-quality and partially obscured labels. For example, the vision-language model recognizes that "Panadol" printed next to a red logo corresponds to "Paracetamol 500 mg," enabling accurate mapping even when text is partly blurred.

In an alternative exemplary embodiment, the data extracting subsystem 312 is also configured with a unit-count estimation model associated with the one or more AI models. The unit-count estimation model is configured to identify and quantify individual healthcare supply units present within the multi-perspective healthcare supply images. The unit-count estimation model allows the system 100 to determine the number of pills, tablets, capsules, and dosage units by detecting boundaries. The unit-count estimation model processes the multi-perspective healthcare images, detects unit-level features such as shape, size, and intensity contrast, and generates the healthcare supply count data. The unit-count estimation model separates visually distinct units and resolves overlapping units. For example, when the blister pack of ten tablets with two empty cavities is inspected, the unit-count estimation model identifies eight tablet instances and outputs the healthcare supply count data accordingly.

The unit-count estimation model is trained using a large dataset of labelled healthcare supply images, where each healthcare supply image is annotated with unit boundaries representing individual pills and dosage forms. Training includes preprocessing steps such as normalization, contrast enhancement, noise reduction, and contour sharpening to improve unit separability. The unit-count estimation model learns to distinguish between various dosage forms, including circular tablets, elongated capsules, chewable tablets, coated pills, and embossed units.

During training, the unit-count estimation model is exposed to diverse imaging variations, including multiple orientations, blister reflections, partial occlusions, shadows, and variations in pill color or surface texture. Over time, the unit-count estimation model learns to reliably identify individual units even in visually challenging scenarios, such as partially consumed blister packs and loose pills with overlapping edges. Once trained, the unit-count estimation model receives the multi-perspective healthcare supply images as input and outputs the healthcare supply count data representing the number of intact units present in the healthcare supply, enabling the system 100 to classify the healthcare supply as one of: full, partially consumed, and nominal consumed during categorization. This pill-counting process is executed once the healthcare supply is positioned in the inspection chamber 112.

As shown in FIG. 6, at step 602, the healthcare supply metadata extraction process begins. At step 604, the at least one healthcare supply is dropped into the inspection chamber 112. The inspection chamber 112 is V-shaped (not limited to), which naturally orients the at least one healthcare supply into a stable and predictable orientation relative to the one or more inspection image capturing units 124. At step 606, once the at least one healthcare supply is placed in the inspection chamber 112, the system 100 assesses whether the orientation of the at least one healthcare supply is suitable for capturing label data. At step 608, if reorientation is required, the system 100 re-engages the pickup logic. At step 610, when the orientation is appropriate, the one or more inspection image capturing units 124 capture the images of the at least one healthcare supply from multiple perspectives.

At step 612, the captured images serve as input to the data extraction subsystem 312 to identify and extract structured healthcare supply metadata. At step 614, the extracted metadata undergoes a crosscheck process against a pre-configured medicine database associated with the one or more databases 216. This ensures accuracy and consistency with known drug identifiers. At step 616, once validated, the metadata extraction process concludes.

In an exemplary embodiment, the manipulator triggering subsystem 308 is configured to modify the control command based on the orientation data to change the orientation of the at least one healthcare supply using the one or more robotic manipulators 104. This adjustment enables the system 100 to capture additional multi-perspective healthcare supply images when the previously captured images are inadequate for extracting the healthcare supply metadata.

Modifying the control command ensures that the one or more robotic manipulators 104 adapt the motion trajectory and motion plan in real-time to reorient the at least one healthcare supply for optimal imaging. For example, instead of moving directly to drop the at least one healthcare supply in the predefined storage chamber 116, the control command is updated to rotate the at least one healthcare supply clockwise by 45° so that the one or more inspection image capturing units 124 may capture the full expiry date.

The inadequate images do not provide sufficient clarity, completeness, and visibility of the label to allow reliable extraction of the healthcare supply metadata. For instance, if the image shows the label with partial glare obscuring the expiry date, the image is flagged as inadequate, and the system 100 rotates the at least one healthcare supply for a new capture.

In an exemplary embodiment, the data mapping subsystem 314 is configured to map the extracted healthcare supply metadata with the storage chamber metadata associated with the plurality of storage chambers 116 to determine the predefined storage chamber 116 for receiving the at least one healthcare supply. This mapping ensures accurate categorization of the unsegregated healthcare supplies based on the user-defined sorting rules and the storage chamber metadata. The storage chamber metadata is pre-assigned digital information describing the category and rule set associated with each storage chamber 116.

The data mapping subsystem 314 is further configured to perform the mapping by comparing the extracted healthcare supply metadata against the storage chamber metadata using, but not constricted to, at least one of: a direct string-matching procedure, a barcode matching procedure, a QR code matching procedure, a numerical matching procedure, a fuzzy logic-based matching procedure of textual data, and the like.

The direct string-matching procedure is a method where textual metadata (e.g., healthcare supply name) from the extracted healthcare supply data is compared character-for-character against the storage chamber metadata. The direct string-matching procedure provides exact, rule-based allocation when the labels exactly match. For example, the extracted text "Amoxicillin 250 mg" matches exactly with the storage chamber metadata "Amoxicillin 250 mg," assigning this healthcare supply to the predefined storage chamber 116.

The barcode matching procedure is a comparison method where a barcode value scanned from the healthcare supply is matched with pre-stored barcode values in the storage chamber metadata. The barcode matching procedure enables precise identification of the at least one healthcare supply through globally unique machine-readable identifiers. The barcode matching procedure enables precise identification of the at least one healthcare supply by decoding one-dimensional machine-readable identifiers, such as Code-128 formats, printed on the packaging. These barcodes provide globally unique product information, such as manufacturer identity, supply type, and variant, allowing the system 100 to link the extracted healthcare supply metadata with the storage chamber metadata. For example, when the barcode on a pill bottle is scanned, the system 100 retrieves the exact medicine name, dosage, and manufacturer details, ensuring accurate categorization and traceability within the pre-defined storage chamber 116. For example, the barcode "8901234567890" from the healthcare supply matches the barcode metadata of the storage chamber 7, leading to the assignment there.

The QR code matching procedure is similar to the barcode matching procedure but uses the QR codes, which can store larger sets of encoded metadata such as product codes and batch numbers. The QR code matching procedure increases robustness of mapping by leveraging dense machine-readable data. By decoding the dense machine-readable data stored within the QR codes, the system 100 enhances the robustness and reliability of the mapping process, as the QR codes provide error correction capabilities and high data density. For instance, even if a portion of the QR code on the blister pack is partially damaged and smudged, the QR code matching procedure can still retrieve the encoded information accurately, thereby improving the consistency and accuracy of healthcare supply categorization. For example, the QR code on the pill bottle encodes Drug ID: D456, Lot No: 789, which matches the storage chamber metadata of storage chamber #12 with the corresponding compartment number.

The numerical matching procedure is a matching process where numeric values, such as dosage strength and lot numbers, are compared against the storage chamber metadata. The numerical matching procedure ensures allocation based on numeric ranges and exact equality. For example, the extracted expiry date "12/2023" is matched to a chamber rule "Expiry≤12/2023," directing the healthcare supply to a trash storage chamber 114.

The fuzzy logic-based matching procedure is a method that tolerates variations, spelling differences, and partial mismatches in the textual data to probabilistically assign the at least one healthcare supply. Unlike strict string matching, which requires exact correspondence, the fuzzy logic-based matching procedure determines a closest match between the extracted healthcare supply metadata and the storage chamber metadata. The fuzzy logic-based matching procedure reduces rejection of valid healthcare supplies caused by OCR errors and inconsistent labeling. For example, extracted text "Amoxicillin" (OCR spelling) is matched to "Amoxicillin" in the storage chamber metadata with 95% similarity confidence.

In another exemplary embodiment, the data mapping subsystem 314 is dynamic and adaptable, capable of continuously updating and refining a mapping logic based on evolving healthcare supply metadata and storage chamber metadata. The data mapping subsystem 314 performs a dynamic mapping based on the extracted healthcare supply metadata. If a first instance of the healthcare supply is detected, the healthcare supply is dynamically assigned to a random storage chamber 116, and all subsequent occurrences of the same healthcare supplies are placed in that storage chamber 116. This ensures there is no fixed mapping between the plurality of storage chambers 116 and the healthcare supplies.

In some exemplary embodiments, the storage chamber metadata may be established using one of: the user-defined sorting rules prior to initiation of the sorting cycle, and dynamically assigned in real time during the sorting cycle to optimize storage allocation within the system 100. For certain users, the mapping between the healthcare supplies and the plurality of storage chambers 116 is fixed; for example, the healthcare supplies A, B, and C may always be routed to a storage chamber 1, while the healthcare supplies D and E are routed to a storage chamber 2. In this configuration, a single storage chamber 116 may contain multiple healthcare supply names or dosages, provided they satisfy the user-defined sorting rules, and the assignment remains constant throughout the sorting cycle.

In contrast, other users may prefer grouping identical one or more healthcare supplies together during each sorting cycle. For example, all "Ibuprofen 200 mg" may be directed to a single storage chamber 116. In such cases, the system 100 assigns the plurality of storage chambers 116 dynamically; any storage chamber 116 that is unassigned at the start of the sorting cycle is automatically designated for the next unique healthcare supply encountered. This dynamic assignment continues until all plurality of storage chambers 116 have been allocated to unique healthcare supplies for that cycle, allowing the system 100 to adapt chamber assignments based on the specific mix of healthcare supplies received.

In an exemplary embodiment, the data mapping subsystem 314 is further configured to assign the at least one healthcare supply to a default storage chamber 116 designated for the unrecognized healthcare supplies when metadata correlation is absent. The default storage chamber 116 is employed for storing the at least one healthcare supply whose metadata cannot be correlated with any existing storage chamber metadata. The default storage chamber 116 prevents system stoppage and misclassification by providing a safe fallback location for the unrecognized healthcare supplies. For example, a new healthcare supply without metadata in the one or more databases 216 is placed into the default storage chamber 116 until manually categorized.

The data mapping subsystem 314 is further configured to assign the at least one healthcare supply to the trash storage chamber 114 if the extracted healthcare supply metadata indicates the at least one healthcare supply is one of: expired, damaged, excluded from restocking based on supply characteristics, and nominal consumed. The trash storage chamber 114 is assigned for expired and unusable healthcare supplies. For example, situations where the healthcare supply is physically damaged (e.g., torn blister cavities, cracked vials, or deformed packaging), nominally consumed/partially utilized (e.g., blister packs with one or more units already removed), and excluded from restocking due to supply characteristics such as missing labels, incomplete metadata, improper sealing, low cost, and noncompliance with restocking criteria. In these scenarios, the system 100 automatically identifies that the healthcare supply cannot be placed back into active storage chambers 116 intended for redistribution. Accordingly, the trash storage chamber 114 is designated to receive the healthcare supplies that are expired or otherwise unsuitable for dispensing and reuse. The trash storage chamber 114 ensures that any such healthcare supplies are reliably isolated from usable inventory, preventing accidental redistribution. The trash storage chamber 114 ensures expired healthcare supplies are segregated to avoid dispensing and reuse. For example, the blister pack showing expiry "03/2022" is automatically routed to the trash storage chamber 114.

Henceforth, the healthcare supplies may be discarded for several reasons, such as being expired or nearing expiry, having insufficient remaining units, exhibiting damaged or compromised packaging, not meeting the restocking criteria defined by a pharmacy, or being associated with a low-cost value. These rules and thresholds vary across different pharmacies, with some considering expiry windows (e.g., 30 or 60 days) or minimum pill-count requirements. The system 100 is configured to accommodate these varying operational policies by dynamically applying pharmacy-specific discard rules. This ensures consistent, rule-based segregation of the healthcare supplies that are not eligible for restocking and reuse.

In an exemplary embodiment, the chamber actuating subsystem 316 is configured to operate the chamber positioning mechanism 118 to actuate the predefined storage chamber 116 into the access position for receiving the at least one healthcare supply. This actuation is carried out based on mapping analysis performed by the data mapping subsystem 314 between the extracted healthcare supply metadata and the storage chamber metadata.

The manipulator triggering subsystem 308 is further configured to generate the control command to trigger the one or more actuators 106 for providing motion to the one or more robotic manipulators 104 based on the positional data associated with the predefined storage chamber 116. This ensures accurate placement of the at least one healthcare supply into the predefined storage chamber 116 once the predefined storage chamber 116 is in the access position. The process integrates metadata analysis, chamber actuation, and manipulator placement to ensure each healthcare supply is categorized correctly. The system 100 enables smooth end-to-end automation, from recognizing the label to physically storing the corresponding healthcare supply.

For example, a vial labeled "Insulin, Expiry: 2025" is matched with storage chamber #7 metadata. The chamber actuating subsystem 316 actuates the storage chamber #7 into the access position using the linear sliding mechanism. The manipulator triggering subsystem 308 generates the control commands for the one or more actuators 106 to move the sorting robotic manipulator 104b towards the storage chamber #7. The sorting robotic manipulator 104b releases the vial into the storage chamber #7, completing categorization.

As shown in FIG. 7, at step 702, the system 100 determines the appropriate storage chamber 116 within the plurality of storage chambers 116 for the at least one healthcare supply. This assignment is based on the user-defined sorting rules.

At step 704, the sorting robotic manipulator 104b begins moving toward the inspection chamber 112 where the at least one healthcare supply is temporarily held. At step 706, in parallel, the chamber positioning mechanism 118 actuates the selected storage chamber 116 into the access position. At step 708, once positioned, the sorting robotic manipulator 104b executes the pickup logic to grip the at least one healthcare supply from the inspection chamber 112. At step 710, after the successful pickup, the sorting robotic manipulator 104b moves toward the predefined storage chamber 116 that is positioned in the access position. The sorting robotic manipulator 104b then releases the healthcare supply into the predefined storage chamber 116 in a controlled manner, ensuring proper placement and preventing damage.

In certain embodiments, upon completion of the sorting process, the system 100 automatically generates a detailed report summarizing all the healthcare supplies processed during the session. The detailed report provides essential information such as names of the healthcare supplies, the quantity detected through unit-count analysis, and the corresponding expiry date extracted from the label regions. The system 100 also documents the exact storage chamber 116 or category to which each healthcare supply has been assigned, allowing the one or more users to track placement and inventory distribution with clarity. Beyond the immediate sorting results, the detailed report includes historical trends and analytical insights, such as frequently discarded healthcare supplies, commonly restocked healthcare supplies, expiry-pattern observations, and usage distributions over time. These analytics assist the one or more users in understanding inventory movement, optimizing restocking strategies, and making data-driven decisions for improved pharmacy operations.

FIG. 8A-8C illustrates an exemplary flow chart of a method 800 for categorizing the unsegregated healthcare supplies into the predefined storage chambers using the healthcare supply metadata, in accordance with an embodiment of the present disclosure.

According to another exemplary embodiment of the present disclosure, the method 800 for categorizing the unsegregated healthcare supplies into the predefined storage chambers using the healthcare supply metadata is disclosed. At step 802, the method 800 includes receiving the unsegregated healthcare supplies into the input container. The input container is configured to hold, organize, and retain the unsegregated healthcare supplies. This step 802 establishes the starting point for automated identification, inspection, and categorization of the unsegregated healthcare supplies.

At step 804, the method 800 includes moving the one or more robotic manipulators configured with the one or more actuators, the one or more end-effectors, and the one or more manipulator image capturing units. The one or more robotic manipulators provide the at least three degrees of freedom to enable precise gripping and releasing of the at least one healthcare supply. This step 804 ensures controlled handling and transfer of the at least one healthcare supply from the unsegregated healthcare supplies for further inspection.

At step 806, the method 800 includes inspecting the at least one healthcare supply in the inspection chamber. The inspection chamber provides a controlled environment with transparent material and multi-perspective imaging capability. This step 806 enables accurate extraction of the healthcare supply metadata.

At step 808, the method 800 includes capturing the multi-perspective healthcare supply images of the at least one healthcare supply positioned on the inspection chamber. The multi-perspective healthcare supply images are captured by the one or more inspection image capturing units placed at defined angles. This step 408 ensures comprehensive visual coverage for accurate metadata extraction.

At step 810, the method 800 includes obtaining multiple categories of operational data by the one or more hardware processors through the data obtaining subsystem. This includes: a) the positional data associated with the one or more robotic manipulators and the predefined storage chambers, b) the color data and the depth data from the one or more manipulator image capturing units and the one or more inspection image capturing units, c) the multi-perspective healthcare supply images and the orientation data from the one or more inspection image capturing units, d) the storage chamber metadata associated with the plurality of storage chambers, e) and the pressure sensor data associated with the one or more end-effectors. This step 810 enables the system to collect all necessary inputs for precise control, analysis, and categorization.

At step 812, the method 800 includes generating the control command through the manipulator triggering subsystem. The control command is based on the positional data, the color data, and the depth data to guide the one or more robotic manipulators. This step 812 enables the one or more actuators to precisely move toward the at least one healthcare supply in the input container.

At step 814, the method 800 includes operating the one or more end-effectors through the end-effector actuation subsystem. The operation is guided by the pressure sensor data, which provides feedback on the gripping force and the vacuum levels. Based on this feedback, the one or more end-effectors perform gripping of the at least one healthcare supply from the input container and from the inspection chamber. The end-effector actuation subsystem also controls the release of the at least one healthcare supply into the inspection chamber and the predefined storage chambers. This step ensures secure transfer and placement of the healthcare supplies while minimizing handling errors.

At step 816, the method 800 includes processing the multi-perspective healthcare supply images through the data extraction subsystem. The data extraction subsystem employs the one or more AI models. This step 816 enables the extraction of the healthcare supply metadata.

At step 818, the method 800 includes modifying the control command through the manipulator triggering subsystem. The modification is guided by the orientation data. Based on the orientation data, the one or more robotic manipulators adjust the orientation of the at least one healthcare supply to a new position and angle. This adjustment allows the capturing of the additional multi-perspective images that provide clearer and previously hidden label information. As a result, the system ensures complete and accurate extraction of the healthcare supply metadata.

At step 820, the method 800 includes mapping the extracted healthcare supply metadata with the storage chamber metadata associated with the plurality of storage chambers using the data mapping subsystem. This mapping is configured to determine the predefined storage chambers to receive the at least one healthcare supply. This step 820 ensures accurate determination of the predefined storage chambers to receive the at least one healthcare supply.

At step 822, the method 800 includes operating the chamber positioning mechanism through the chamber actuating subsystem. The chamber positioning mechanism is actuated to bring the predefined storage chambers into the access position. This actuation is based on the mapping analysis between the extracted healthcare supply metadata and the storage chamber metadata. The step 822 ensures the correct storage chamber is made ready to receive the identified at least one healthcare supply.

At step 824, the method 800 includes generating the control command through the manipulator triggering subsystem. The control command is used to trigger the one or more actuators for controlled motion of the one or more robotic manipulators. This step 824 prepares the one or more robotic manipulators to transfer the at least one healthcare supply toward the predefined storage chambers.

At step 826, the method 800 includes providing the motion to the one or more robotic manipulators through the manipulator triggering subsystem. The motion is guided by the positional data associated with the predefined storage chambers. Using this control, the one or more robotic manipulators release the at least one healthcare supply into the identified predefined storage chambers. This step 826 completes the categorization of the unsegregated healthcare supplies.

In FIG. 8A-8C, the circular symbol with "F and G" written inside is being used as an off-page connector. This is used for indicating that FIG. 8A continues in the subsequent pages as FIGS. 8B and 8C.

Numerous advantages of the present disclosure may be apparent from the discussion above. In accordance with the present disclosure, the system for categorizing the unsegregated healthcare supplies into the predefined storage chambers using the healthcare supply metadata is disclosed. By combining low-cost one or more robotic manipulators, suction-based picking, compact sliding storage chambers, and the one or more AI models, the system automates a process that is currently manual, repetitive, and time-consuming, freeing pharmacy staff to focus on higher-value tasks. The system provides unique advantages over existing pharmacy automation systems by automating the sorting of returned healthcare supplies and reading label text to extract critical details such as expiry dates. The system is compact, affordable, and easily deployable in existing pharmacies. The system reduces errors, improves efficiency, and frees the pharmacy staff to focus on higher-value clinical work. useful for sorting the unsegregated healthcare supplies in hospital pharmacies, long-term care pharmacies, medicine redistribution centers, reverse distributors, and medical waste processing facilities.

The system is a compact, cost-effective device capable of sorting the unsegregated healthcare supplies in various form factors such as unit doses, pill packs, vials, syringes, inhalers, 14/30 day blister cards, and non-healthcare items that may be considered trash. Barcode scanning may be integrated into the imaging workflow by decoding the barcodes and the QR codes directly from RGB images of the at least one healthcare supply. This removes the need for a separate barcode scanner.

A description of an embodiment with several components in communication with each other does not imply that all such components are required. On the contrary, a variety of optional components are described to illustrate the wide variety of possible embodiments of the invention. When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of the more than one device or article, or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open-ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

We claim:

1. A system for categorizing unsegregated healthcare supplies into predefined storage chambers using healthcare supply metadata, the system comprising:

an input container configured to receive and retain the unsegregated healthcare supplies;

one or more robotic manipulators configured with one or more actuators, one or more end-effectors, and one or more manipulator image capturing units, to move in at least three degrees of freedom for gripping and releasing at least one healthcare supply from the unsegregated healthcare supplies in the input container;

an inspection chamber operatively positioned proximate to the input container, configured to receive the at least one healthcare supply from the input container through the one or more robotic manipulators for inspecting the at least one healthcare supply for extracting the healthcare supply metadata;

one or more inspection image capturing units operatively positioned at one or more defined angles with reference to the inspection chamber, configured to capture multi-perspective healthcare supply images of the at least one healthcare supply positioned on the inspection chamber;

a plurality of storage chambers operatively positioned proximate to one of the input container or the inspection chamber, each storage chamber of the plurality of storage chambers operatively coupled to a chamber positioning mechanism configured to selectively position the predefined storage chambers within the plurality of storage chambers into an access position for receiving the at least one healthcare supply from the one or more robotic manipulators;

one or more hardware processors;

a non-transitory memory unit operatively connected to the one or more hardware processors, wherein the non-transitory memory unit comprises a set of computer-readable instructions in form of a plurality of subsystems, configured to be executed by the one or more hardware processors, wherein the plurality of subsystems comprises:

a data obtaining subsystem configured to obtain positional data associated with the one or more robotic manipulators and the predefined storage chambers, color data and depth data from the one or more manipulator image capturing units, the multi-perspective healthcare supply images and orientation data from the one or more inspection image capturing units, storage chamber metadata associated with the plurality of storage chambers, and pressure sensor data associated with the one or more end-effectors;

a manipulator triggering subsystem configured to generate a control command to trigger the one or more actuators for providing a motion to the one or more robotic manipulators based on the positional data, the color data and the depth data to reach towards the at least one healthcare supply in the input container;

an end-effector actuation subsystem configured to operate the one or more end-effectors based on the pressure sensor data for performing gripping the at least one healthcare supply from the input container and the inspection chamber, and releasing the at least one healthcare supply in the inspection chamber and the predefined storage chambers;

a data extraction subsystem configured with one or more artificial intelligence (AI) models to process the multi-perspective healthcare supply images for extracting the healthcare supply metadata;

the manipulator triggering subsystem configured to modify the control command based on the orientation data to change an orientation of the at least one healthcare supply using the one or more robotic manipulators, to capture additional multi-perspective healthcare supply images if the multi-perspective healthcare supply images are inadequate for extracting the healthcare supply metadata;

a data mapping subsystem configured to map the extracted healthcare supply metadata with the storage chamber metadata associated with the plurality of storage chambers to determine the predefined storage chambers for receiving the at least one healthcare supply;

a chamber actuating subsystem configured to operate the chamber positioning mechanism to actuate the predefined storage chambers into the access position for receiving the at least one healthcare supply based on mapping analysis performed by the data mapping subsystem, between the extracted healthcare supply metadata and the storage chamber metadata; and the manipulator triggering subsystem configured to:

generate the control command to trigger the one or more actuators; and cause the one or more actuators to provide the motion to the one or more robotic manipulators based on the positional data associated with the predefined storage chambers for releasing the at least one healthcare supply into the predefined storage chambers to categorize the unsegregated healthcare supplies.

2. The system of claim 1, wherein the one or more actuators comprise at least one of: a stepper motor, a servo motor, a linear actuator, a pneumatic actuator, and a hydraulic actuator.

3. The system of claim 1, wherein the one or more end-effectors comprise at least one of: a suction-based gripper, a mechanical gripper, and a hybrid gripper.

4. The system of claim 1, wherein the at least three degrees of freedom provided by the one or more actuators operatively coupled to a mechanical transmission assembly configured to generate the motion across multiple axes, the mechanical transmission assembly comprises at least one of: manipulator assembly, linkages, gear trains, cam systems, differential mechanisms, clutches, timing belts, and timing pulleys.

5. The system of claim 1, wherein the one or more manipulator image capturing units and the one or more inspection image capturing units comprise at least one of: a Red-Green-Blue (RGB) camera, a Red-Green-Blue with Depth (RGB-D) camera, a depth sensor, a stereo vision camera, a multi-spectral imaging camera, and a thermal imaging camera.

6. The system of claim 1, wherein the inspection chamber is formed of a transparent material selected from a group comprises one of: glass, acrylic, polycarbonate, and transparent polymer, for enabling unobstructed multi-perspective imaging of the at least one healthcare supply by the one or more inspection image capturing units; and the inspection chamber operatively coupled to a rotating mechanism configured to rotate the inspection chamber about a predetermined axis for capturing the multi-perspective healthcare supply images of the at least one healthcare supply.

7. The system of claim 1, wherein each storage chamber of the plurality of storage chambers configured with a unique chamber identifier, each storage chamber with the unique chamber identifier mapped with the storage chamber metadata, the storage chamber metadata comprises at least one of: a healthcare supply name, a dosage strength, a lot number, an expiry date, a manufacturer identifier, a barcode value, a quick response (QR) code value, and a healthcare supply category identifier, generated based on user-defined sorting rules input through a user interface.

8. The system of claim 1, wherein the chamber positioning mechanism comprises at least one of: a linear sliding mechanism, a rotary carousel mechanism, a scissor-lift mechanism, a spring-loaded pop-out mechanism, and an elevator mechanism.

9. The system of claim 1, wherein the positional data is obtained from one or more of: encoder feedback signals generated by encoders operatively associated with the one or more actuators, limit switch signals defining reference positions of the one or more robotic manipulators and the chamber positioning mechanism, step count data generated by actuator drives of the one or more actuators, and the depth data captured by the one or more manipulator image capturing units.

10. The system of claim 1, wherein the manipulator triggering subsystem further configured to:

process the positional data using a mathematical representation model to determine a current location of the one or more robotic manipulators;

process the color data and the depth data using a vision-based object detection model associated with the one or more artificial intelligence (AI) models to determine a target location of the at least one healthcare supply within the input container; and generate the control command by computing a motion trajectory from the current location to the target location using a motion planning model associated with the one or more artificial intelligence (AI) models, the motion planning model comprising at least one of: an inverse kinematics solver, a trajectory optimization model, and a reinforcement learning-based motion policy.

11. The system of claim 1, wherein the end-effector actuation subsystem is further configured to:

process the pressure sensor data by monitoring one of: vacuum levels in the suction-based gripper and gripping force in the mechanical gripper, to compare the monitored one of: the vacuum levels and the gripping force against predefined threshold values to verify successful gripping and releasing of the at least one healthcare supply; and modify the control command to initiate one of: a re-grasp sequence and a repositioning sequence based on:

the pressure sensor data indicating one of: an ineffective gripping and releasing; and comparative analysis between one of: the vacuum levels and the gripping force against the predefined threshold values, the predefined threshold values generated based on historical pressure sensor data associated with gripping of the unsegregated healthcare supplies.

12. The system of claim 1, wherein the one or more artificial intelligence (AI) models in the data extraction subsystem comprises at least one of:

an image segmentation model trained to segment label region on the multi-perspective healthcare supply images from nearby packaging information;

an object detection model trained to localize alphanumeric text within the segmented label regions to extract the healthcare supply metadata;

an optical character recognition (OCR) model trained to extract the alphanumeric text from the multi-perspective healthcare supply images;

a barcode or quick response (QR) code recognition model to decode machine-readable identifiers for extracting the healthcare supply metadata;

a vision-language model configured to interpret at least one of: textual features and visual features in combination to extract the healthcare supply metadata; and a unit-count estimation model configured to identify healthcare supply boundaries within the multi-perspective healthcare supply images for generating healthcare supply count data based on the identified healthcare supply boundaries.

13. The system of claim 1, wherein the data mapping subsystem further configured to:

perform the mapping by comparing the extracted healthcare supply metadata against the storage chamber metadata using at least one of: direct string-matching procedure, barcode matching procedure, quick response (QR) code matching procedure, numerical matching procedure, and fuzzy logic-based matching procedure of textual data; and assign the at least one healthcare supply to a default storage chamber within the plurality of storage chambers designated for unrecognized healthcare supplies if metadata correlation is absent between the extracted healthcare supply metadata and the storage chamber metadata; and assign the at least one healthcare supply to a trash storage chamber within the plurality of storage chambers if the extracted healthcare supply metadata indicates the at least one healthcare supply is one of: expired, damaged, excluded from restocking based on supply characteristics, and nominal consumed.

14. A method for categorizing unsegregated healthcare supplies into predefined storage chambers using healthcare supply metadata, the method comprising:

receiving, in an input container, the unsegregated healthcare supplies;

moving one or more robotic manipulators configured with one or more actuators, one or more end-effectors, and one or more manipulator image capturing units, at least three degrees of freedom to grip and release at least one healthcare supply within the unsegregated healthcare supplies;

inspecting, in an inspection chamber, the at least one healthcare supply from the input container to extract the healthcare supply metadata;

capturing, by one or more inspection image capturing units, multi-perspective healthcare supply images of the at least one healthcare supply positioned on the inspection chamber;

obtaining, by one or more hardware processors through a data obtaining subsystem, positional data associated with the one or more robotic manipulators and the predefined storage chambers, color data and depth data from the one or more manipulator image capturing units and the one or more inspection image capturing units, the multi-perspective healthcare supply images and orientation data from the one or more inspection image capturing units, storage chamber metadata associated with a plurality of storage chambers, and pressure sensor data associated with the one or more end-effectors;

generating, by the one or more hardware processors through a manipulator triggering subsystem, a control command to trigger the one or more actuators for providing the motion to the one or more robotic manipulators based on the positional data, the color data and the depth data to reach towards the at least one healthcare supply in the input container;

operating, by the one or more hardware processors through an end-effector actuation subsystem, the one or more end-effectors based on the pressure sensor data to perform gripping of the at least one healthcare supply from the input container and the inspection chamber, and releasing the at least one healthcare supply in the inspection chamber and the predefined storage chambers;

processing, by the one or more hardware processors through a data extraction subsystem with one or more artificial intelligence (AI) models, the multi-perspective healthcare supply images to extract the healthcare supply metadata;

modifying, by the one or more hardware processors through the manipulator triggering subsystem, the control command based on the orientation data to change an orientation of the at least one healthcare supply using the one or more robotic manipulators, to capture additional multi-perspective healthcare supply images if the multi-perspective healthcare supply images are inadequate to extract the healthcare supply metadata;

mapping, by the one or more hardware processors through a data mapping subsystem, the extracted healthcare supply metadata with the storage chamber metadata associated with the plurality of storage chambers to determine the predefined storage chambers to receive the at least one healthcare supply;

operating, by the one or more hardware processors through a chamber actuating subsystem, the chamber positioning mechanism to actuate the predefined storage chambers into the access position for receiving the at least one healthcare supply based on mapping analysis performed by the data mapping subsystem, between the extracted healthcare supply metadata and the storage chamber metadata;

generating, by the one or more hardware processors through the manipulator triggering subsystem, the control command to trigger the one or more actuators; and providing, by the one or more hardware processors through the manipulator triggering subsystem, the motion to the one or more robotic manipulators based on the positional data associated with the predefined storage chambers to release the at least one healthcare supply into the predefined storage chambers to categorize the unsegregated healthcare supplies.

15. The method of claim 14, further comprises:

generating, through a user interface, user-defined sorting rules to map the storage chamber metadata with a unique chamber identifier associated with each storage chamber of the plurality of storage chambers, the storage chamber metadata comprises at least one of: a healthcare supply name, a dosage strength, a lot number, an expiry date, a manufacturer identifier, a barcode value, a quick response (QR) code value, and a healthcare supply category identifier.

16. The method of claim 14, further comprises:

processing, by the one or more hardware processors through the manipulator triggering subsystem, the positional data using a mathematical representation model to determine a current location of the one or more robotic manipulators;

processing, by the one or more hardware processors through the manipulator triggering subsystem, the color data and the depth data using a vision-based object detection model associated with the one or more artificial intelligence (AI) models to determine a target location of the at least one healthcare supply within the input container; and generating, by the one or more hardware processors through the manipulator triggering subsystem, the control command by computing a motion trajectory from the current location to the target location using a motion planning model associated with the one or more artificial intelligence (AI) models, the motion planning model comprising at least one of: an inverse kinematics solver, a trajectory optimization model, and a reinforcement learning-based motion policy.

17. The method of claim 14, further comprises:

processing, by the one or more hardware processors through the end-effector actuation subsystem, the pressure sensor data by monitoring one of: vacuum levels in the suction-based gripper and gripping force in the mechanical gripper to compare the monitored one of: the vacuum levels and the gripping force against predefined threshold values to verify successful gripping and releasing of the at least one healthcare supply; and modifying, by the one or more hardware processors through the end-effector actuation subsystem, the control command to initiate one of: a re-grasp sequence and a repositioning sequence based on:

the pressure sensor data indicating one of: an ineffective gripping and releasing; and comparative analysis between one of: the vacuum levels and the gripping force against the predefined threshold values, the predefined threshold values generated based on historical pressure sensor data associated with gripping of the unsegregated healthcare supplies.

18. The method of claim 14, wherein the one or more artificial intelligence (AI) models in the data extraction subsystem comprises at least one of:

an image segmentation model trained to segment label region on the multi-perspective healthcare supply images from nearby packaging information;

an object detection model trained to localize alphanumeric text within the segmented label regions to extract the healthcare supply metadata;

an optical character recognition (OCR) model trained to extract the alphanumeric text from the multi-perspective healthcare supply images;

a barcode or quick response (QR) code recognition model to decode machine-readable identifiers for extracting the healthcare supply metadata;

a vision-language model configured to interpret at least one of: textual features and visual features in combination to extract the healthcare supply metadata; and a unit-count estimation model configured to identify healthcare supply boundaries within the multi-perspective healthcare supply images for generating healthcare supply count data based on the identified healthcare supply boundaries.

19. The method of claim 14, further comprises:

performing, by the one or more hardware processors through the data mapping subsystem, the mapping by comparing the extracted healthcare supply metadata against the storage chamber metadata using at least one of: direct string-matching procedure, barcode matching procedure, quick response (QR) code matching procedure, numerical matching procedure, and fuzzy logic-based matching procedure of textual data; and assigning, by the one or more hardware processors through the data mapping subsystem, the at least one healthcare supply to a default storage chamber within the plurality of storage chambers designated for unrecognized healthcare supplies if metadata correlation is absent between the extracted healthcare supply metadata and the storage chamber metadata; and assigning, by the one or more hardware processors through the data mapping subsystem, the at least one healthcare supply to a trash storage chamber within the plurality of storage chambers if the extracted healthcare supply metadata indicates the at least one healthcare supply is one of: expired, damaged, excluded from restocking based on supply characteristics, and nominal consumed.

20. A non-transitory computer-readable storage medium storing computer-readable instructions that, when executed by one or more hardware processors, cause the one or more hardware processors to perform operations for categorizing unsegregated healthcare supplies into predefined storage chambers using healthcare supply metadata, the operations comprising:

obtaining positional data associated with one or more robotic manipulators and the predefined storage chambers, color data and depth data from one or more manipulator image capturing units and one or more inspection image capturing units, multi-perspective healthcare supply images and orientation data from the one or more inspection image capturing units, storage chamber metadata associated with a plurality of storage chambers, and pressure sensor data associated with one or more end-effectors;

generating a control command to trigger one or more actuators for providing motion to the one or more robotic manipulators based on the positional data, the color data and the depth data to reach towards at least one healthcare supply within the unsegregated healthcare supplies in an input container;

operating the one or more end-effectors based on the pressure sensor data to perform gripping of the at least one healthcare supply from the input container and an inspection chamber, and releasing the at least one healthcare supply in the inspection chamber and the predefined storage chambers within the plurality of storage chambers;

processing with one or more artificial intelligence (AI) models the multi-perspective healthcare supply images to extract the healthcare supply metadata;

modifying the control command based on the orientation data to change an orientation of the at least one healthcare supply using the one or more robotic manipulators, to capture additional multi-perspective healthcare supply images if the multi-perspective healthcare supply images are inadequate to extract the healthcare supply metadata;

mapping the extracted healthcare supply metadata with the storage chamber metadata associated with the plurality of storage chambers to determine the predefined storage chambers to receive the at least one healthcare supply;

operating the chamber positioning mechanism to actuate the predefined storage chambers into an access position for receiving the at least one healthcare supply based on mapping analysis between the extracted healthcare supply metadata and the storage chamber metadata;

generating the control command to trigger the one or more actuators; and providing the motion to the one or more robotic manipulators based on the positional data associated with the predefined storage chambers to release the at least one healthcare supply into the predefined storage chambers to categorize the unsegregated healthcare supplies.

* * * * *